(12) United States Patent
Boisvert et al.

(10) Patent No.: US 11,887,722 B2
(45) Date of Patent: *Jan. 30, 2024

(54) METHODS AND SYSTEMS FOR IMPROVING INFECTION CONTROL IN A BUILDING

(71) Applicant: Honeywell International Inc., Charlotte, NC (US)

(72) Inventors: David Boisvert, North Chelmsford, MA (US); David Rausch, Charlotte, NC (US); Armin Wellig, Charlotte, NC (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 187 days.

This patent is subject to a terminal disclaimer.

(21) Appl. No.: 17/196,297

(22) Filed: Mar. 9, 2021

(65) Prior Publication Data

US 2021/0193309 A1 Jun. 24, 2021

Related U.S. Application Data

(63) Continuation of application No. 16/246,437, filed on Jan. 11, 2019, now Pat. No. 10,978,199.

(51) Int. Cl.
*G16H 40/20* (2018.01)
*G05B 15/02* (2006.01)
(Continued)

(52) U.S. Cl.
CPC .............. *G16H 40/20* (2018.01); *G05B 15/02* (2013.01); *G08B 21/182* (2013.01); *H04L 67/125* (2013.01)

(58) Field of Classification Search
CPC ........ G16H 40/20; G16H 50/80; G16H 50/00; G16H 50/20; G16H 40/67; G16H 50/30;
(Continued)

(56) References Cited

U.S. PATENT DOCUMENTS

| 191,512 A | 6/1877 | Bennett et al. |
| 4,009,647 A | 3/1977 | Howorth |

(Continued)

FOREIGN PATENT DOCUMENTS

| CA | 2387100 A1 | 11/2003 |
| CA | 2538139 A1 | 3/2005 |

(Continued)

OTHER PUBLICATIONS

"Energy Manager User Guide," Release 3.2, Honeywell, 180 pages, 2008.

(Continued)

*Primary Examiner* — Hai Phan
*Assistant Examiner* — Anthony D Afrifa-Kyei
(74) *Attorney, Agent, or Firm* — Seager, Tufte & Wickhem, LLP

(57) ABSTRACT

A building management system (BMS) for a medical facility that includes a plurality of rooms with at least one of the rooms having a plurality of sensors. An elevated infection risk determination system is operatively coupled to the plurality of sensors for determining when an elevated infection risk occurs in one or more of the rooms. The BMS may include a memory for storing one or more programmable infection risk compliance parameters, an input port for receiving an elevated infection risk alert for the particular room in the medical facility, a control port for providing control commands to one or more building components of the building management system, and a controller. The controller may be configured to provide control commands via the control port in response to receiving the elevated infection risk alert for the particular room based at least in part on one or more programmable infection risk compliance parameters to help mitigate the elevated infection risk in the particular room.

20 Claims, 8 Drawing Sheets

(51) Int. Cl.
*G08B 21/18* (2006.01)
*H04L 67/125* (2022.01)

(58) Field of Classification Search
CPC ........ G16H 40/00; G16H 10/60; G16H 40/63; G16H 50/70; G16H 70/60; G05B 15/02; G08B 21/182; G08B 21/245; H04L 67/125; G06V 10/28; G06V 20/64; G06V 40/161
See application file for complete search history.

(56) References Cited

U.S. PATENT DOCUMENTS

| | | | |
|---|---|---|---|
| 4,375,637 A | 3/1983 | Desjardins |
| 4,918,615 A | 4/1990 | Suzuki et al. |
| 4,939,922 A | 7/1990 | Smalley et al. |
| 5,566,084 A | 10/1996 | Cmar |
| 5,727,579 A | 3/1998 | Chardack |
| 5,745,126 A | 4/1998 | Jain et al. |
| 5,751,916 A | 5/1998 | Kon et al. |
| 5,777,598 A | 7/1998 | Gowda et al. |
| 5,973,662 A | 10/1999 | Singers et al. |
| 6,065,842 A | 5/2000 | Fink |
| 6,139,177 A | 10/2000 | Venkatraman et al. |
| 6,144,993 A | 11/2000 | Fukunaga et al. |
| 6,157,943 A | 12/2000 | Meyer |
| 6,229,429 B1 | 5/2001 | Horon |
| 6,238,337 B1 | 5/2001 | Kambhatla et al. |
| 6,334,211 B1 | 12/2001 | Kojima et al. |
| 6,353,853 B1 | 3/2002 | Gravlin |
| 6,369,695 B2 | 4/2002 | Horon |
| 6,375,038 B1 | 4/2002 | Daansen et al. |
| 6,429,868 B1 | 8/2002 | Dehner, Jr. et al. |
| 6,473,084 B1 | 10/2002 | Phillips et al. |
| 6,487,457 B1 | 11/2002 | Hull et al. |
| 6,580,950 B1 | 6/2003 | Johnson et al. |
| 6,598,056 B1 | 7/2003 | Hull et al. |
| 6,619,555 B2 | 9/2003 | Rosen |
| 6,704,012 B1 | 3/2004 | Lefave |
| 6,720,874 B2 | 4/2004 | Fufido et al. |
| 6,741,915 B2 | 5/2004 | Poth |
| 6,796,896 B2 | 9/2004 | Laiti |
| 6,801,199 B1 | 10/2004 | Wallman |
| 6,816,878 B1 | 11/2004 | Zimmers et al. |
| 6,876,951 B2 | 4/2005 | Skidmore et al. |
| 6,882,278 B2 | 4/2005 | Winings et al. |
| 6,904,385 B1 | 6/2005 | Budike, Jr. |
| 6,907,387 B1 | 6/2005 | Reardon |
| 6,911,177 B2 | 6/2005 | Deal |
| 6,993,403 B1 | 1/2006 | Dadebo et al. |
| 6,993,417 B2 | 1/2006 | Osann, Jr. |
| 7,023,440 B1 | 4/2006 | Havekost et al. |
| 7,031,880 B1 | 4/2006 | Seem et al. |
| 7,062,722 B1 | 6/2006 | Carlin et al. |
| 7,110,843 B2 | 9/2006 | Pagnano et al. |
| 7,139,685 B2 | 11/2006 | Bascle et al. |
| 7,164,972 B2 | 1/2007 | Imhof et al. |
| 7,183,899 B2 | 2/2007 | Behnke |
| 7,200,639 B1 | 4/2007 | Yoshida |
| 7,222,111 B1 | 5/2007 | Budike, Jr. |
| 7,222,800 B2 | 5/2007 | Wruck |
| 7,257,397 B2 | 8/2007 | Shamoon et al. |
| 7,280,030 B1 | 10/2007 | Monaco |
| 7,292,908 B2 | 11/2007 | Borne et al. |
| 7,295,116 B2 | 11/2007 | Kumar et al. |
| 7,302,313 B2 | 11/2007 | Sharp et al. |
| 7,308,323 B2 | 12/2007 | Kruk et al. |
| 7,308,388 B2 | 12/2007 | Beverina et al. |
| 7,313,447 B2 | 12/2007 | Hsiung et al. |
| 7,346,433 B2 | 3/2008 | Budike, Jr. |
| 7,356,548 B1 | 4/2008 | Culp et al. |
| 7,379,782 B1 | 5/2008 | Cocco |
| 7,383,148 B2 | 6/2008 | Ahmed |
| 7,434,742 B2 | 10/2008 | Mueller et al. |
| 7,447,333 B1 | 11/2008 | Masticola et al. |
| 7,466,224 B2 | 12/2008 | Ward et al. |
| 7,496,472 B2 | 2/2009 | Seem |
| 7,512,450 B2 | 3/2009 | Ahmed |
| 7,516,490 B2 | 4/2009 | Riordan et al. |
| 7,548,833 B2 | 6/2009 | Ahmed |
| 7,551,092 B1 | 6/2009 | Henry |
| 7,557,729 B2 | 7/2009 | Hubbard et al. |
| 7,567,844 B2 | 7/2009 | Thomas et al. |
| 7,596,473 B2 | 9/2009 | Hansen et al. |
| 7,610,910 B2 | 11/2009 | Ahmed |
| 7,626,507 B2 | 12/2009 | LaCasse |
| 7,664,574 B2 | 2/2010 | Imhof et al. |
| 7,682,464 B2 | 3/2010 | Glenn et al. |
| 7,702,421 B2 | 4/2010 | Sullivan et al. |
| 7,729,882 B2 | 6/2010 | Seem |
| 7,755,494 B2 | 7/2010 | Melker et al. |
| 7,761,310 B2 | 7/2010 | Rodgers |
| 7,774,227 B2 | 8/2010 | Srivastava |
| 7,797,188 B2 | 9/2010 | Srivastava |
| 7,819,136 B1 | 10/2010 | Eddy |
| 7,822,806 B2 | 10/2010 | Frank et al. |
| 7,856,370 B2 | 12/2010 | Katta et al. |
| 7,978,083 B2 | 7/2011 | Melker et al. |
| 7,984,384 B2 | 7/2011 | Chaudhri et al. |
| 7,986,323 B2 | 7/2011 | Kobayashi et al. |
| 8,024,666 B2 | 9/2011 | Thompson |
| 8,086,047 B2 | 12/2011 | Penke et al. |
| 8,099,178 B2 | 1/2012 | Mairs et al. |
| 8,151,280 B2 | 4/2012 | Sather et al. |
| 8,176,095 B2 | 5/2012 | Murray et al. |
| 8,218,871 B2 | 7/2012 | Angell et al. |
| 8,219,660 B2 | 7/2012 | McCoy et al. |
| 8,271,941 B2 | 9/2012 | Zhang et al. |
| 8,294,585 B2 | 10/2012 | Barnhill |
| 8,302,020 B2 | 10/2012 | Louch et al. |
| 8,320,634 B2 | 11/2012 | Deutsch |
| 8,334,422 B2 | 12/2012 | Gutsol et al. |
| 8,344,893 B1 | 1/2013 | Drammeh |
| 8,375,118 B2 | 2/2013 | Hao et al. |
| 8,473,080 B2 | 6/2013 | Seem et al. |
| 8,476,590 B2 | 7/2013 | Stratmann et al. |
| 8,516,016 B2 | 8/2013 | Park et al. |
| 8,558,660 B2 | 10/2013 | Nix et al. |
| 8,639,527 B2 | 1/2014 | Rensvold et al. |
| 8,698,637 B2 | 4/2014 | Raichman |
| 8,816,860 B2 | 8/2014 | Ophardt et al. |
| 8,869,027 B2 | 10/2014 | Louch et al. |
| 8,904,497 B2 | 12/2014 | Hsieh |
| 8,936,944 B2 | 1/2015 | Peltz et al. |
| 8,947,437 B2 | 2/2015 | Garr et al. |
| 8,950,019 B2 | 2/2015 | Loberger et al. |
| 9,000,926 B2 | 4/2015 | Hollock et al. |
| 9,002,532 B2 | 4/2015 | Asmus |
| 9,030,325 B2 | 5/2015 | Taneff |
| 9,098,738 B2 | 8/2015 | Bilet et al. |
| 9,105,071 B2 | 8/2015 | Fletcher et al. |
| 9,175,356 B2 | 11/2015 | Peltz et al. |
| 9,235,657 B1 | 1/2016 | Wenzel et al. |
| 9,240,111 B2 | 1/2016 | Scott et al. |
| 9,256,702 B2 | 2/2016 | Elbsat et al. |
| 9,280,884 B1 | 3/2016 | Schultz et al. |
| 9,292,972 B2 | 3/2016 | Hailemariam et al. |
| 9,320,662 B2 | 4/2016 | Hayes et al. |
| 9,322,566 B2 | 4/2016 | Wenzel et al. |
| 9,355,069 B2 | 5/2016 | Elbsat et al. |
| 9,370,600 B1 | 6/2016 | DuPuis et al. |
| 9,373,242 B1 | 6/2016 | Conrad et al. |
| 9,396,638 B2 | 7/2016 | Wildman et al. |
| 9,311,807 B2 | 8/2016 | Schultz et al. |
| 9,406,212 B2 | 8/2016 | De Luca et al. |
| 9,418,535 B1 | 8/2016 | Felch et al. |
| 9,418,536 B1 | 8/2016 | Felch et al. |
| 9,436,179 B1 | 9/2016 | Turney et al. |
| 9,449,219 B2 | 9/2016 | Bilet et al. |
| 9,477,543 B2 | 10/2016 | Henley et al. |
| 9,497,832 B2 | 11/2016 | Verberkt et al. |
| 9,513,364 B2 | 12/2016 | Hall et al. |
| 9,526,380 B2 | 12/2016 | Hamilton et al. |
| 9,526,806 B2 | 12/2016 | Park et al. |

(56) References Cited

U.S. PATENT DOCUMENTS

| | | | |
|---|---|---|---|
| 9,536,415 B2 | 1/2017 | De Luca et al. |
| 9,558,648 B2 | 1/2017 | Douglas |
| 9,568,204 B2 | 2/2017 | Asmus et al. |
| 9,581,985 B2 | 2/2017 | Walser et al. |
| 9,591,267 B2 | 3/2017 | Tipton et al. |
| 9,606,520 B2 | 3/2017 | Noboa et al. |
| 9,612,601 B2 | 4/2017 | Beyhaghi et al. |
| 9,613,518 B2 | 4/2017 | Dunn et al. |
| 9,618,224 B2 | 4/2017 | Emmons et al. |
| 9,640,059 B2 | 5/2017 | Hyland |
| 9,672,360 B2 | 6/2017 | Barkan |
| 9,696,054 B2 | 7/2017 | Asmus |
| 9,710,700 B2 | 7/2017 | Bilet et al. |
| 9,715,242 B2 | 7/2017 | Pillai et al. |
| 9,721,452 B2 | 8/2017 | Felch et al. |
| 9,729,945 B2 | 8/2017 | Schultz et al. |
| 9,778,639 B2 | 10/2017 | Boettcher et al. |
| 9,784,464 B2 | 10/2017 | Yamamoto et al. |
| 9,798,336 B2 | 10/2017 | Przybylski |
| 9,843,743 B2 | 12/2017 | Lewis et al. |
| 9,852,481 B1 | 12/2017 | Turney et al. |
| 9,856,634 B1 | 1/2018 | Rodenbeck et al. |
| 9,872,088 B2 * | 1/2018 | Fadell ............ H04Q 9/00 |
| 9,875,639 B2 | 1/2018 | Bone et al. |
| 9,911,312 B2 | 3/2018 | Wildman et al. |
| 9,940,819 B2 | 4/2018 | Ferniany |
| 9,956,306 B2 | 5/2018 | Brais et al. |
| 9,982,903 B1 | 5/2018 | Ridder et al. |
| 9,986,175 B2 | 5/2018 | Frank et al. |
| 10,007,259 B2 | 6/2018 | Turney et al. |
| 10,055,114 B2 | 8/2018 | Shah et al. |
| 10,071,177 B1 | 9/2018 | Kellogg, Jr. |
| 10,087,608 B2 | 10/2018 | Dobizl et al. |
| 10,101,730 B2 | 10/2018 | Wenzel et al. |
| 10,101,731 B2 | 10/2018 | Asmus et al. |
| 10,175,681 B2 | 1/2019 | Wenzel et al. |
| 10,222,083 B2 | 3/2019 | Drees et al. |
| 10,223,894 B2 | 3/2019 | Raichman |
| 10,228,837 B2 | 3/2019 | Hua et al. |
| 10,235,865 B2 | 3/2019 | Thyroff |
| 10,251,610 B2 | 4/2019 | Parthasarathy et al. |
| 10,282,796 B2 | 5/2019 | Elbsat et al. |
| 10,288,306 B2 | 5/2019 | Ridder et al. |
| 10,303,843 B2 | 5/2019 | Bitran et al. |
| 10,317,864 B2 | 6/2019 | Boettcher et al. |
| 10,332,382 B2 | 6/2019 | Thyroff |
| 10,359,748 B2 | 7/2019 | Elbsat et al. |
| 10,386,820 B2 | 8/2019 | Wenzel et al. |
| 10,402,767 B2 | 9/2019 | Noboa et al. |
| 10,514,178 B2 | 12/2019 | Willmott et al. |
| 10,514,817 B2 | 12/2019 | Hua et al. |
| 10,520,210 B2 | 12/2019 | Park et al. |
| 10,544,955 B2 | 1/2020 | Przybylski |
| 10,558,178 B2 | 2/2020 | Willmott et al. |
| 10,559,180 B2 | 2/2020 | Pourmohammad et al. |
| 10,559,181 B2 | 2/2020 | Pourmohammad et al. |
| 10,565,844 B2 | 2/2020 | Pourmohammad et al. |
| 10,600,263 B2 | 3/2020 | Park et al. |
| 10,602,474 B2 | 3/2020 | Goldstein |
| 10,605,477 B2 | 3/2020 | Ridder |
| 10,607,147 B2 | 3/2020 | Raykov et al. |
| 10,619,882 B2 | 4/2020 | Chatterjee et al. |
| 10,627,124 B2 | 4/2020 | Walser et al. |
| 10,673,380 B2 | 6/2020 | Wenzel et al. |
| 10,678,227 B2 | 6/2020 | Przybylski et al. |
| 10,706,375 B2 | 7/2020 | Wenzel et al. |
| 10,726,711 B2 | 7/2020 | Subramanian et al. |
| 10,732,584 B2 | 8/2020 | Elbsat et al. |
| 10,767,885 B2 | 9/2020 | Przybylski et al. |
| 10,775,988 B2 | 9/2020 | Narain et al. |
| 10,796,554 B2 | 10/2020 | Vincent et al. |
| 10,809,682 B2 | 10/2020 | Patil et al. |
| 10,809,705 B2 | 10/2020 | Przybylski |
| 10,824,125 B2 | 11/2020 | Elbsat et al. |
| 10,854,194 B2 | 12/2020 | Park et al. |
| 10,871,298 B2 | 12/2020 | Ridder et al. |
| 10,876,754 B2 | 12/2020 | Wenzel et al. |
| 10,890,904 B2 | 1/2021 | Turney et al. |
| 10,900,686 B2 | 1/2021 | Willmott et al. |
| 10,901,446 B2 | 1/2021 | Nesler et al. |
| 10,909,642 B2 | 2/2021 | Elbsat et al. |
| 10,915,094 B2 | 2/2021 | Wenzel et al. |
| 10,917,740 B1 | 2/2021 | Scott et al. |
| 10,921,972 B2 | 2/2021 | Park et al. |
| 10,921,973 B2 | 2/2021 | Park et al. |
| 10,928,790 B2 | 2/2021 | Mueller et al. |
| 10,948,884 B2 | 3/2021 | Beaty et al. |
| 10,949,777 B2 | 3/2021 | Elbsat et al. |
| 10,955,800 B2 | 3/2021 | Burroughs et al. |
| 10,956,842 B2 | 3/2021 | Wenzel et al. |
| 10,962,945 B2 | 3/2021 | Park et al. |
| 10,969,135 B2 | 4/2021 | Willmott et al. |
| 11,002,457 B2 | 5/2021 | Turney et al. |
| 11,009,252 B2 | 5/2021 | Turney et al. |
| 11,010,846 B2 | 5/2021 | Elbsat et al. |
| 11,016,648 B2 | 5/2021 | Fala et al. |
| 11,016,998 B2 | 5/2021 | Park et al. |
| 11,022,947 B2 | 6/2021 | Elbsat et al. |
| 11,024,292 B2 | 6/2021 | Park et al. |
| 11,036,249 B2 | 6/2021 | Elbsat |
| 11,038,709 B2 | 6/2021 | Park et al. |
| 11,042,139 B2 | 6/2021 | Deshpande et al. |
| 11,042,924 B2 | 6/2021 | Asmus et al. |
| 11,061,424 B2 | 7/2021 | Elbsat et al. |
| 11,068,821 B2 | 7/2021 | Wenzel et al. |
| 11,070,389 B2 | 7/2021 | Schuster et al. |
| 11,073,976 B2 | 7/2021 | Park et al. |
| 11,080,289 B2 | 8/2021 | Park et al. |
| 11,080,426 B2 | 8/2021 | Park et al. |
| 11,086,276 B2 | 8/2021 | Wenzel et al. |
| 11,094,186 B2 | 8/2021 | Razak |
| 11,108,587 B2 | 8/2021 | Park et al. |
| 11,131,473 B2 | 8/2021 | Risbeck et al. |
| 11,113,295 B2 | 9/2021 | Park et al. |
| 11,119,458 B2 | 9/2021 | Asp et al. |
| 11,120,012 B2 | 9/2021 | Park et al. |
| 11,150,617 B2 | 10/2021 | Ploegert et al. |
| 11,151,983 B2 | 10/2021 | Park et al. |
| 11,156,996 B2 | 10/2021 | Schuster et al. |
| 11,158,306 B2 | 10/2021 | Park et al. |
| 11,182,047 B2 | 11/2021 | Nayak et al. |
| 11,195,401 B2 | 12/2021 | Pourmohammad |
| 11,217,087 B2 | 1/2022 | Pelski |
| 11,226,126 B2 | 1/2022 | Przybylski et al. |
| 11,243,523 B2 | 2/2022 | Llopis et al. |
| 11,268,715 B2 | 3/2022 | Park et al. |
| 11,268,996 B2 | 3/2022 | Vitullo et al. |
| 11,269,505 B2 | 3/2022 | Fala et al. |
| 11,272,011 B1 | 3/2022 | Laughton et al. |
| 11,272,316 B2 | 3/2022 | Scott et al. |
| 11,275,348 B2 | 3/2022 | Park et al. |
| 11,275,363 B2 | 3/2022 | Przybylski et al. |
| 11,281,169 B2 | 3/2022 | Chatterjee et al. |
| 11,288,754 B2 | 3/2022 | Elbsat et al. |
| 11,314,726 B2 | 4/2022 | Park et al. |
| 11,314,788 B2 | 4/2022 | Park et al. |
| 11,334,044 B2 | 5/2022 | Goyal |
| 11,353,834 B2 | 6/2022 | Mueller et al. |
| 11,356,292 B2 | 6/2022 | Ploegert et al. |
| 11,360,451 B2 | 6/2022 | Pancholi et al. |
| 11,361,123 B2 | 6/2022 | Ploegert et al. |
| 2002/0111698 A1 | 8/2002 | Graziano et al. |
| 2002/0130868 A1 | 9/2002 | Smith |
| 2003/0028269 A1 | 2/2003 | Spriggs et al. |
| 2003/0030637 A1 | 2/2003 | Grinstein et al. |
| 2003/0046862 A1 | 3/2003 | Wolf et al. |
| 2003/0071814 A1 | 4/2003 | Jou et al. |
| 2003/0078677 A1 | 4/2003 | Hull et al. |
| 2003/0083957 A1 | 5/2003 | Olefson |
| 2003/0103075 A1 | 6/2003 | Rosselot |
| 2003/0171851 A1 | 9/2003 | Brickfield et al. |
| 2003/0214400 A1 | 11/2003 | Mizutani et al. |
| 2003/0233432 A1 | 12/2003 | Davis et al. |
| 2004/0001009 A1 | 1/2004 | Winings et al. |

(56) References Cited

U.S. PATENT DOCUMENTS

| | | |
|---|---|---|
| 2004/0064260 A1 | 4/2004 | Padmanabhan et al. |
| 2004/0143474 A1 | 7/2004 | Haeberle et al. |
| 2004/0153437 A1 | 8/2004 | Buchan |
| 2004/0168115 A1 | 8/2004 | Bauernschmidt et al. |
| 2004/0233192 A1 | 11/2004 | Hopper |
| 2004/0260411 A1 | 12/2004 | Cannon |
| 2005/0010460 A1 | 1/2005 | Mizoguchi et al. |
| 2005/0119767 A1 | 6/2005 | Kiwimagi et al. |
| 2005/0143863 A1 | 6/2005 | Ruane et al. |
| 2005/0267900 A1 | 12/2005 | Ahmed et al. |
| 2006/0004841 A1 | 1/2006 | Heikkonen et al. |
| 2006/0009862 A1 | 1/2006 | Imhof et al. |
| 2006/0017547 A1 | 1/2006 | Buckingham et al. |
| 2006/0020177 A1 | 1/2006 | Seo et al. |
| 2006/0028471 A1 | 2/2006 | Kincaid et al. |
| 2006/0029256 A1 | 2/2006 | Miyoshi et al. |
| 2006/0058900 A1 | 3/2006 | Johanson et al. |
| 2006/0067545 A1 | 3/2006 | Lewis et al. |
| 2006/0067546 A1 | 3/2006 | Lewis et al. |
| 2006/0077255 A1 | 4/2006 | Cheng |
| 2006/0184326 A1 | 8/2006 | McNally et al. |
| 2006/0231568 A1 | 10/2006 | Lynn et al. |
| 2006/0265664 A1 | 11/2006 | Simons et al. |
| 2006/0279630 A1 | 12/2006 | Aggarwal et al. |
| 2007/0016955 A1 | 1/2007 | Goldberg et al. |
| 2007/0055757 A1 | 3/2007 | Mairs et al. |
| 2007/0055760 A1 | 3/2007 | McCoy et al. |
| 2007/0061046 A1 | 3/2007 | Mairs et al. |
| 2007/0067062 A1 | 3/2007 | Mairs et al. |
| 2007/0088534 A1 | 4/2007 | MacArthur et al. |
| 2007/0090951 A1 | 4/2007 | Chan et al. |
| 2007/0091091 A1 | 4/2007 | Gardiner et al. |
| 2007/0101433 A1 | 5/2007 | Louch et al. |
| 2007/0114295 A1 | 5/2007 | Jenkins |
| 2007/0120652 A1 | 5/2007 | Behnke |
| 2007/0139208 A1 | 6/2007 | Kates |
| 2007/0216682 A1 | 9/2007 | Navratil et al. |
| 2007/0219645 A1 | 9/2007 | Thomas et al. |
| 2007/0239484 A1 | 10/2007 | Arond et al. |
| 2007/0268122 A1 | 11/2007 | Kow et al. |
| 2008/0001763 A1 | 1/2008 | Raja et al. |
| 2008/0027885 A1 | 1/2008 | Van Putten et al. |
| 2008/0036593 A1 | 2/2008 | Rose-Pehrsson et al. |
| 2008/0062167 A1 | 3/2008 | Boggs et al. |
| 2008/0099045 A1 | 5/2008 | Glenn et al. |
| 2008/0103798 A1 | 5/2008 | Domenikos et al. |
| 2008/0120396 A1 | 5/2008 | Jayaram et al. |
| 2008/0144885 A1 | 6/2008 | Zucherman et al. |
| 2008/0183424 A1 | 7/2008 | Seem |
| 2008/0194009 A1 | 8/2008 | Marentis |
| 2008/0198231 A1 | 8/2008 | Ozdemir et al. |
| 2008/0209342 A1 | 8/2008 | Taylor et al. |
| 2008/0222565 A1 | 9/2008 | Taylor et al. |
| 2008/0224862 A1 | 9/2008 | Cirker |
| 2008/0242945 A1 | 10/2008 | Gugliotti et al. |
| 2008/0250800 A1 | 10/2008 | Wetzel |
| 2008/0279420 A1 | 11/2008 | Masticola et al. |
| 2008/0280275 A1 | 11/2008 | Collopy |
| 2008/0303658 A1 | 12/2008 | Melker et al. |
| 2008/0306985 A1 | 12/2008 | Murray et al. |
| 2008/0320552 A1 | 12/2008 | Kumar et al. |
| 2009/0001181 A1 | 1/2009 | Siddaramanna et al. |
| 2009/0024944 A1 | 1/2009 | Louch et al. |
| 2009/0065596 A1 | 3/2009 | Seem et al. |
| 2009/0083120 A1 | 3/2009 | Strichman et al. |
| 2009/0096791 A1 | 4/2009 | Abshear et al. |
| 2009/0125337 A1 | 5/2009 | Abri |
| 2009/0125825 A1 | 5/2009 | Rye et al. |
| 2009/0144023 A1 | 6/2009 | Seem |
| 2009/0157744 A1 | 6/2009 | McConnell |
| 2009/0160673 A1 | 6/2009 | Cirker |
| 2009/0322782 A1 | 12/2009 | Kimchi et al. |
| 2010/0048167 A1 | 2/2010 | Chow et al. |
| 2010/0058248 A1 | 3/2010 | Park |
| 2010/0064001 A1 | 3/2010 | Daily |
| 2010/0070089 A1 | 3/2010 | Harrod et al. |
| 2010/0073162 A1 | 3/2010 | Johnson et al. |
| 2010/0123560 A1 | 5/2010 | Nix et al. |
| 2010/0134296 A1 | 6/2010 | Hwang |
| 2010/0156628 A1 | 6/2010 | Ainsbury et al. |
| 2010/0156630 A1 | 6/2010 | Ainsbury |
| 2010/0188228 A1 | 7/2010 | Hyland |
| 2010/0223198 A1 | 9/2010 | Noureldin et al. |
| 2010/0249955 A1 | 9/2010 | Sitton |
| 2010/0286937 A1 | 11/2010 | Hedley et al. |
| 2010/0318200 A1 | 12/2010 | Foslien et al. |
| 2010/0324962 A1 | 12/2010 | Nesler et al. |
| 2011/0010654 A1 | 1/2011 | Raymond et al. |
| 2011/0057799 A1 | 3/2011 | Taneff |
| 2011/0077779 A1 | 3/2011 | Fuller et al. |
| 2011/0083094 A1 | 4/2011 | Laycock et al. |
| 2011/0087988 A1 | 4/2011 | Ray et al. |
| 2011/0112854 A1 | 5/2011 | Koch et al. |
| 2011/0126111 A1 | 5/2011 | Gill et al. |
| 2011/0154426 A1 | 6/2011 | Doser et al. |
| 2011/0161124 A1 | 6/2011 | Lappinga et al. |
| 2011/0169646 A1 | 7/2011 | Raichman |
| 2011/0184563 A1 | 7/2011 | Foslien et al. |
| 2011/0202467 A1 | 8/2011 | Hilber et al. |
| 2011/0273298 A1 | 11/2011 | Snodgrass et al. |
| 2011/0291841 A1 | 12/2011 | Hollock et al. |
| 2011/0298301 A1 | 12/2011 | Wong et al. |
| 2011/0316703 A1 | 12/2011 | Butler et al. |
| 2011/0320054 A1 | 12/2011 | Brzezowski |
| 2012/0022700 A1 | 1/2012 | Drees et al. |
| 2012/0039503 A1 | 2/2012 | Chen et al. |
| 2012/0062382 A1 | 3/2012 | Taneff |
| 2012/0075464 A1 | 3/2012 | Derenne et al. |
| 2012/0109988 A1 | 5/2012 | Li et al. |
| 2012/0112883 A1* | 5/2012 | Wallace ............... G16H 50/80 340/10.1 |
| 2012/0131217 A1 | 5/2012 | Delorme et al. |
| 2012/0158185 A1 | 6/2012 | El-Mankabady et al. |
| 2012/0216243 A1 | 8/2012 | Gill et al. |
| 2012/0224057 A1 | 9/2012 | Gill et al. |
| 2012/0259466 A1 | 10/2012 | Ray et al. |
| 2012/0262472 A1 | 10/2012 | Garr et al. |
| 2012/0272146 A1 | 10/2012 | D'souza et al. |
| 2012/0291068 A1 | 11/2012 | Khushoo et al. |
| 2012/0303652 A1 | 11/2012 | Tseng |
| 2012/0310418 A1 | 12/2012 | Harrod et al. |
| 2013/0055132 A1 | 2/2013 | Foslien |
| 2013/0060794 A1 | 3/2013 | Puttabasappa et al. |
| 2013/0082842 A1 | 4/2013 | Balazs et al. |
| 2013/0085609 A1 | 4/2013 | Barker |
| 2013/0086152 A1 | 4/2013 | Hersche et al. |
| 2013/0091631 A1 | 4/2013 | Tayes et al. |
| 2013/0110295 A1 | 5/2013 | Zheng et al. |
| 2013/0169681 A1 | 7/2013 | Rasane et al. |
| 2013/0184880 A1 | 7/2013 | McMahon |
| 2013/0187775 A1 | 7/2013 | Marsden et al. |
| 2013/0204570 A1 | 8/2013 | Mendelson et al. |
| 2013/0229276 A1 | 9/2013 | Hunter |
| 2013/0268293 A1 | 10/2013 | Knudson et al. |
| 2013/0289774 A1 | 10/2013 | Day et al. |
| 2013/0309154 A1 | 11/2013 | Call et al. |
| 2014/0032157 A1 | 1/2014 | Khiani |
| 2014/0040998 A1 | 2/2014 | Hsieh |
| 2014/0046490 A1 | 2/2014 | Foslien et al. |
| 2014/0046722 A1 | 2/2014 | Rosenbloom et al. |
| 2014/0058539 A1 | 2/2014 | Park |
| 2014/0167917 A2 | 6/2014 | Wallace et al. |
| 2014/0207291 A1 | 7/2014 | Golden et al. |
| 2014/0292518 A1 | 10/2014 | Wildman et al. |
| 2014/0307076 A1 | 10/2014 | Deutsch |
| 2014/0309757 A1 | 10/2014 | Le Sant et al. |
| 2014/0316582 A1 | 10/2014 | Berg-Sonne et al. |
| 2014/0320289 A1 | 10/2014 | Raichman |
| 2014/0342724 A1 | 11/2014 | Hill et al. |
| 2015/0025329 A1* | 1/2015 | Amarasingham ...... G16H 50/20 600/300 |
| 2015/0032264 A1 | 1/2015 | Emmons et al. |
| 2015/0056909 A1 | 2/2015 | Chien |
| 2015/0070174 A1 | 3/2015 | Douglas |

(56) References Cited

U.S. PATENT DOCUMENTS

| | | | |
|---|---|---|---|
| 2015/0077258 A1 | 3/2015 | Nelson et al. | |
| 2015/0113462 A1 | 4/2015 | Chen et al. | |
| 2015/0153918 A1 | 6/2015 | Chen et al. | |
| 2015/0161874 A1 | 6/2015 | Thyroff et al. | |
| 2015/0167995 A1 | 6/2015 | Fadell et al. | |
| 2015/0168949 A1 | 6/2015 | Hua et al. | |
| 2015/0194043 A1 | 7/2015 | Dunn et al. | |
| 2015/0198707 A1 | 7/2015 | Al-Alusi | |
| 2015/0212717 A1 | 7/2015 | Nair et al. | |
| 2015/0213222 A1* | 7/2015 | Amarasingham | G16H 50/30 705/2 |
| 2015/0213379 A1 | 7/2015 | Nair et al. | |
| 2015/0216369 A1 | 8/2015 | Hamilton et al. | |
| 2015/0253748 A1 | 9/2015 | Brun et al. | |
| 2015/0281287 A1 | 10/2015 | Gill et al. | |
| 2016/0061476 A1 | 3/2016 | Schultz et al. | |
| 2016/0061477 A1 | 3/2016 | Schultz et al. | |
| 2016/0061794 A1 | 3/2016 | Schultz et al. | |
| 2016/0061795 A1 | 3/2016 | Schultz et al. | |
| 2016/0063833 A1 | 3/2016 | Schultz et al. | |
| 2016/0066067 A1 | 3/2016 | Schultz et al. | |
| 2016/0116181 A1* | 4/2016 | Aultman | F24F 11/62 700/276 |
| 2016/0139067 A1 | 5/2016 | Grace | |
| 2016/0253897 A1 | 9/2016 | Wildman et al. | |
| 2016/0255516 A1 | 9/2016 | Hill et al. | |
| 2016/0298864 A1 | 10/2016 | Ekolind et al. | |
| 2016/0306934 A1 | 10/2016 | Sperry et al. | |
| 2016/0314683 A1 | 10/2016 | Felch et al. | |
| 2016/0328948 A1 | 11/2016 | Ferniany | |
| 2016/0335731 A1 | 11/2016 | Hall | |
| 2016/0367925 A1 | 12/2016 | Blackley | |
| 2017/0024986 A1 | 1/2017 | Austin | |
| 2017/0193792 A1 | 7/2017 | Bermudez Rodriguez et al. | |
| 2017/0256155 A1 | 9/2017 | Sengstaken, Jr. | |
| 2017/0280949 A1 | 10/2017 | Wildman et al. | |
| 2017/0294106 A1 | 10/2017 | Thyroff | |
| 2017/0365024 A1 | 12/2017 | Koch et al. | |
| 2018/0016773 A1 | 1/2018 | Chandler et al. | |
| 2018/0151054 A1 | 5/2018 | Pi | |
| 2018/0218591 A1 | 8/2018 | Easter | |
| 2018/0259927 A1 | 9/2018 | Przybylski et al. | |
| 2018/0293038 A1 | 10/2018 | Meruva et al. | |
| 2018/0301014 A1 | 10/2018 | Worral et al. | |
| 2018/0313695 A1 | 11/2018 | Shim et al. | |
| 2018/0365957 A1 | 12/2018 | Wright et al. | |
| 2019/0051138 A1 | 2/2019 | Easter | |
| 2019/0139395 A1 | 5/2019 | Rogachev et al. | |
| 2019/0209719 A1 | 7/2019 | Andersen et al. | |
| 2020/0009280 A1 | 1/2020 | Kupa et al. | |
| 2020/0074836 A1 | 3/2020 | Kolavennu et al. | |
| 2020/0090089 A1* | 3/2020 | Aston | G06Q 10/0635 |
| 2020/0146557 A1 | 5/2020 | Cheung et al. | |
| 2020/0200420 A1 | 6/2020 | Nayak et al. | |
| 2020/0348038 A1* | 11/2020 | Risbeck | F24F 11/52 |
| 2021/0010701 A1 | 1/2021 | Suindykov et al. | |
| 2021/0011443 A1 | 1/2021 | Mcnamara et al. | |
| 2021/0011444 A1 | 1/2021 | Risbeck et al. | |
| 2021/0364181 A1 | 11/2021 | Risbeck et al. | |
| 2021/0373519 A1 | 12/2021 | Risbeck et al. | |
| 2022/0011731 A1 | 1/2022 | Risbeck et al. | |
| 2022/0113045 A1 | 4/2022 | Gamroth et al. | |
| 2022/0137580 A1 | 5/2022 | Burroughs et al. | |

FOREIGN PATENT DOCUMENTS

| | | |
|---|---|---|
| CA | 2600529 C | 9/2006 |
| CN | 103110410 A | 5/2013 |
| CN | 103970977 A | 8/2014 |
| CN | 105116848 A | 12/2015 |
| CN | 108961714 A | 12/2018 |
| CN | 110009245 A | 7/2019 |
| CN | 110084928 A | 8/2019 |
| CN | 110827457 A | 2/2020 |
| EP | 1669912 A1 | 6/2006 |
| EP | 2310981 A1 | 4/2011 |
| JP | 7085166 A | 3/1995 |
| JP | 11024735 A | 1/1999 |
| JP | 11317936 A | 11/1999 |
| JP | 2001356813 A | 12/2001 |
| JP | 2005242531 A | 9/2005 |
| JP | 2005311563 A | 11/2005 |
| KR | 1172747 B1 | 8/2012 |
| KR | 101445367 B1 | 10/2014 |
| KR | 1499081 B1 | 3/2015 |
| WO | 9621264 A3 | 11/1996 |
| WO | 2004029518 A1 | 4/2004 |
| WO | 2005045715 A2 | 5/2005 |
| WO | 2008152433 A1 | 12/2008 |
| WO | 2008157755 A1 | 12/2008 |
| WO | 2009012319 A2 | 1/2009 |
| WO | 2009079648 A1 | 6/2009 |
| WO | 2010106474 A1 | 9/2010 |
| WO | 2011025085 A1 | 3/2011 |
| WO | 2011043732 A1 | 4/2011 |
| WO | 2011057173 A2 | 5/2011 |
| WO | 2011123743 A1 | 10/2011 |
| WO | 2013062725 A1 | 5/2013 |
| WO | 2013178819 A1 | 12/2013 |
| WO | 2014009291 A1 | 1/2014 |
| WO | 2014098861 A1 | 6/2014 |
| WO | 2014135517 A1 | 9/2014 |
| WO | 2016123536 A1 | 8/2016 |
| WO | 2017057274 A1 | 4/2017 |
| WO | 2019046580 A1 | 3/2019 |
| WO | 2020024553 A1 | 2/2020 |

OTHER PUBLICATIONS

"Fuzzy Logic Toolbox 2.1, Design and Stimulate Fuzzy Logic Systems," The MathWorks, 2 pages, May 2004.
"Junk Charts, Recycling Chartjunk as junk art," 3 pages, Oct. 2, 2006.
"Model Predictive Control Toolbox 2, Develop Internal Model-Based Controllers for Constrained Multivariable Processes," The MathWorks, 4 pages, Mar. 2005.
Honeywell, "Product Guide 2004," XP-002472407, 127 pages, 2004.
"Statistics Toolbox, for Use with Matlab," User's Guide Version2, The MathWorks, 408 pages, Jan. 1999.
"Vykon Energy Suite Student Guide," Tridium Inc., 307 pages, Mar. 3, 2006.
"Web Based Energy Information Systems for Energy Management and Demand Response in Commercial Buildings," California Energy Commission, 80 pages, Oct. 2003.
Andover Controls, Network News, vol. 2, No. 2, 8 pages, 1997.
Andover Controls World, 4 pages, Spring 1997.
Bell, Michael B. et al., "Early Event Detection—Results from A Prototype Implementation," AICHE Spring National Meeting, 15 pages, Apr. 2005.
Cadgraphics, "The Cadgraphics User's Guide," 198 pages, 2003.
Carrier Comfort Network CCN Web, "Web Browser User Interface to the Carrier Comfort Network," 2 pages, 2002.
Carrier Comfort Network CCN Web, Overview and Configuration Manual, 134 pages, Apr. 2006.
Carrier Comfort Network CCN Web, Product Data, 2 pages, Apr. 2006.
Carrier, "i-Vu Powerful and Intuitive Front End for Building Control," 2 pages, Aug. 2005.
Carrier, "i-Vu Web-Based Integrated Control System," 3 pages, 2005.
Carrier, Demo Screen Shots, 15 pages, prior to Aug. 27, 2007.
Carrier, i-Vu CCN 4.0, Owner's Guide, 20 pages, Jul. 2007.
Carrier, i-Vu CCN, 7 pages, 2007.
Chen, Tony. F., "Rank Revealing QR Factorizations," Linear Algebra and It's Applications, vol. 88-89, p. 67-82, Apr. 1987.
Circon, "i-Browse Web-Based Monitoring and Control for Facility Management," 2 pages, prior to Aug. 27, 2007.

(56) References Cited

OTHER PUBLICATIONS

Published Australian Application 2009904740, 28 pages, Application Filed on Sep. 29, 2009.
Echelon, "Energy Control Solutions with the i.Lon SmartServer," 4 pages, 2007.
Echelon, "i.Lon 100e3 Internet Server Models 72101R-300, 72101R-308, 72102R-300, 72103-R300 . . ." 5 pages, copyright 2002-2007.
Echelon, "i.Lon 100e3 Internet Server New Features," 15 pages, Sep. 2006.
Echelon, "i.Lon SmartServer," 5 pages, 2007.
Honeywell News Release, "Honeywell's New Sysnet Facilities Integration System for Boiler Plant and Combustion Safety Processes," 4 pages, Dec. 15, 1995.
Honeywell, "Excel Building Supervisor-Integrated R7044 and FS90 Ver. 2.0," Operator Manual, 70 pages, Apr. 1995.
Honeywell, "Introduction of the S7350A Honeywell WebPAD Information Appliance," Home and Building Control Bulletin, 2 pages, Aug. 29, 2000; Picture of WebPad Device with touch screen, 1 Page; and screen shots of WebPad Device, 4 pages.
Honeywell, Excel 15B W7760B Building Manager Release 2.02.00, Installation Instructions, 28 pages, Dec. 2004.
Honeywell, The RapidZone Solution, Excel 5000 Open System, Application Guide, 52 pages, Jan. 2004.
http://pueblo.lbl.gov/~olken . . . , "Remote Building Monitoring and Operations Home Page," 5 pages, prior to Aug. 27, 2007.
http://www.commercial.carrier.com/commercial/hvac/productdescription . . . , "Carrier: i-Vu CCN," 1 page, printed Mar. 11, 2008.
http://www.commercial.carrier.com/commercial/hvac/productdescription . . . , "Carrier: 33CSCCNWEB-01 CCN Web Internet Connection to the Carrier Comfort Network," 1 page, printed Mar. 11, 2008.
http://www.docs.hvacpartners.com/idc/groups/public/documents/techlit/gs-controls-ivuccn.rtf, "Products," 5 pages, printed Jul. 3, 2007.
http://www.lightstat.com/products/istat.asp, Lightstat Incorporated, "Internet Programmable Communicating Thermostats," 1 page, printed Mar. 13, 2007.
http://www.sharpsystems.com/products/pc_notebooks/actius/rd/3d/, "Actius RD3D Desktop Replacement Notebook with Industry-Breakthrough 3D Screen," Sharp, 1 page, printed Jun. 16, 2005.
http://www2.sims.berkeley.edu/courses/is213/s06/projects/lightson;final.html, "Lights On A Wireless Lighting Control System," 11 pages, printed Mar. 22, 2007.
I.Lon 100e3 Internet Server, 1 page, prior to Aug. 27, 2007.
I.Lon, SmartServer, 2 pages, prior to Aug. 27, 2007.
I-stat, Demo Screen Shots, 9 pages, printed Mar. 13, 2007.
I-stat, The Internet Programmable Thermostat, 2 pages, prior to Aug. 27, 2007.
Jeffrey Ball, "Green Goal of 'Carbon Neutrality' Hits Limit," TheWall Street Journal, 7 pages, Dec. 30, 2008.
Johnson Controls, Network Integration Engine (NIE) 3 pages, Nov. 9, 2007.
Johnson Controls, Network Integration Engine (NIE), Product Bulletin, pp. 1-11, Jan. 30, 2008.
Kourti, Theodora, "Process Analysis and Abnormal Situation Detection: From Theory to Practice," IEEE Control Systems Magazine, p. 10-25, Oct. 2002.
Mathew, Paul A., "Action-Oriented Benchmarking, Using CEUS Date to Identify and Prioritize Efficiency Opportunities in California Commercial Buildings," 26 pages, Jun. 2007.
Morrison, Don et al., "The Early Event Detection Toolkit," Honeywell Process Solutions, 14 pages, Jan. 2006.
Narang, "WEBARC: Control and Monitoring of Building Systems Over the Web," 53 pages, May 1999.
Olken et al., "Object Lessons Learned from a Distributed System for Remote Building Monitoring and Operation," ACM SIGPLAN Notices, vol. 33, No. 10, pp. 284-295, Oct. 1998.
Proliphix, Inc., "Proliphix IP Devices: HTTP API," 28 pages, Jan. 23, 2006.
Proliphix, Inc., Remote Management User Guide, 12 pages, prior to Aug. 27, 2007.
Richard Rogan et al., "Smart and Final Food Stores: A Case Study in Web Based Energy Information and Collection," Web Based Energy Information and Control Systems: Case Studies and Application, Chapter 6, p. 59-64, 2005.
Sharp, "Actius AL3DU 3D LC Display High Performance 3D Visualization," 2 pages, prior to Mar. 17, 2006.
So et al., "Building Automation on the Information Superhighway," ASHRAE (American Society of Heating Refrigerating, and Air Conditioning) Transactions, vol. 104, Part 2, pp. 176-191, 1998.
So et al., "Building Automation Systems on the Internet," Facilities vol. 15, No. 5/6, pp. 125-133, May/Jun. 1997.
Talon, "Raptor Controller," 6 pages, Oct. 2003.
Talon, "Workstation Software," 4 pages, Nov. 2002.
Trane, "System Programming, Tracer Summit Version 14, BMTW-SVP01D-EN," 623 pages, 2002.
Lucid Design Group, Inc., "Building Dashboard," 2 pages, Printed May 30, 2013.
"America's Largest Managed Security Services Provider Launches Comprehensive, Integrated Covid-19 Safety Program for Office Buildings and Suites," KastleSafeSpaces, 5 pages, May 11, 2020.
"Biometric Door Reader With Body Temperature Detection," Kintronics, 9 pages, accessed May 21, 2020.
"Body Surface Temperature Screening with Alarm Function TVS-200IS/TVS-500IS," Nippon Avionics Co., 3 pages, accessed May 21, 2020.
"BriefCam announces video analytics innovation for contact tracing, physical distancing, occupancy management and face mask detection," BriefCam LTD, 11 pages, Jun. 5, 2020.
"Thermal Imaging SmartPhone Can Be used For Temperature Screening of People," CAT, 3 pages, accessed Jul. 13, 2020.
"Contact Tracing Now Available on Identiv's Hirsch Velocity Access Control Platform," IDENTIV, 5 pages, May 21, 2020.
Silva et al., "Cough localization for the detection of respiratory diseases in pig houses," ScienceDirect, 7 pages, May 28, 2008.
Oey et al., "Evaluation of Isolation Compliance Using Real Time Video In Critical Care," North Shore University Hospital, 1 page, Oct. 9, 2015.
"Facial Attendace System With Temperature Screening Now In India," IANS, 5 pages, Mar. 19, 2020.
"Plan to Re-Open," Ehigh, 16 pages, accessed Jun. 13, 2020.
"How Smarter AI-Powered Cameras Can Mitigate the Spread of Wuhan Novel," AnyConnect, 22 pages, 2020.
"How to fight COVID-19 with machine learning," DataRevenue, 20 pages, accessed May 25, 2020.
"Inncontrol 5," Honeywell, 2 pages, Aug. 8, 2018.
"IP Door Access Control," Kintronics, 21 pages, 2014.
"Kogniz AI Health Response Platform," Kogniz, 9 pages, accessed May 21, 2020.
"Machine Learning Could Check If You're Social Distancing Properly at Work," MIT Technology Review, 7 pages, Apr. 17, 2020.
Punn et al., "Monitoring COVID-19 social distancing with person detection and tracking via fine-tuned Yolo v3 and Deepsort techniques," 10 pages, May 6, 2020.
"NEC launches dual face biometric and fever detection system for access control," Biometric Update, 4 pages, May 8, 2020.
"Remote temperature monitoring," Axis Communication, 10 pages, 2014.
"FebriEye—AI Based Thermal Temperature Screening System," vehant, 1 page, 2020.
"See The World In A New Way Hikvision Thermal Cameras," Hikvision, 12 pages, 2017.
Allain, "Trying out the iPhone Infrared Camera: The Flir One," Wired, 15 pages, 2014.
Dasgupta, "Your voice may be able to tell you if you have Covid," Hindustan Times, 4 pages, Apr. 16, 2020.
Ganguty, "Gurugram-based startup Staqu has modified AI-powered Jarvis to battle coronavirus," Yourstory, 7 pages, Mar. 31, 2020.
U.S. Appl. No. 62/739,655, filed Oct. 1, 2018 and entitled "System and Method for Monitoring Compliance With an Optimized Plan in an Operating Room to Reduce Patient Infection".
Johnson Controls Develops Industry-first AI Driven Digital Solution to Manage Clean Air, Energy, Sustainability, Comfort and Cost in Buildings, 7 pages, 2022. Accessed Aug. 29, 2022.

(56) References Cited

OTHER PUBLICATIONS

Johnson Controls and Microsoft Announce Global Collaboration, Launch Integration between Open Blue Digital Twin and Azure Digital Twins, 7 pages, 2022. Accessed Aug. 29, 2022.
Open Blue Companion Desktop User Guide, Johnson Controls, 18 pages, 2022.
Open Blue Digital Twin:Designed for Buildings. Infused with AI, Johnson Controls, 17 pages, 2022. Accessed Aug. 29, 2022.
Open Blue Enterprise Manager User Guide, Johnson Controls, Release 3.1, 72 pages, Jan. 28, 2021.
Open Blue Enterprise Manager User Guide, Johnson Controls, Release 4.0, 78pages, Nov. 29, 2021.
Open Blue Location Manager User Guide, Johnson Controls, Release 2.4.7, 28 pages, Jul. 20, 2022.
Open Blue Enterprise Manager, Optimize Building Portfolio Performance with Advanced Data Analytics and AI, Johnson Controls, 20 pages, Accessed Aug. 29, 2022.
Open Blue Platform, Make Smarter, Faster, More Data-Driven Decisions, Johnson Controls, 15 pages, 2022. Accessed Aug. 29, 2022.
Open Blue, Now, Spaces have Memory and Identity, Johnson Controls, 20 pages, 2022. Accessed Feb. 10, 2022.
Open Blue Enterprise Manager User Guide, Johnson Controls, 108 pages, Release 4.1.3, 2022, Accessed Aug. 29, 2022.
Risbeck et al; "Modeling and Multiobjective Optimization of Indoor Airborne Disease Transmission Risk and Associated Energy Consumption for Building HVAC Systems," Energy and Buildings, vol. 253, 24 pages, 2021.
Sinha et al; "Balance Infection Risk, Sustainability and Comfort with Open Blue," Johnson Controls, 2 pages, 2021.
Iuliana Bocicor et al. "Wireless Sensor Network based System for the Prevention of Hospital Acquired Infections", arxiv.org, Cornell University Ithaca, NY 14853, May 2, 2017, XP080947042, (Abstract).
Shhedi Zaid Ali et al., "Traditional and ICT Solutions for Preventing the Hospital Acquired Infection", 2015 20th International Conference on Control Systems and Computer Science, IEEE, May 27, 2015, pp. 867-873, XP033188038.
Extended European Search Report, EP application No. 20151295.1, pp. 13, May 26, 2020.
U.S. Appl. No. 14/109,496, filed Dec. 17, 2013.
www.geappliances.com/home-energy-manager/about-energy-monitors.htm, "Energy Monitor, Home Energy Monitors, GE Nucleus," 2 pages, printed Jan. 15, 2013.
www.luciddesigngroup.com/network/apps.php#homepage, "Lucid Design Group—Building Dashboard Network—Apps," 7 pages, Jan. 15, 2013.
Preuveneers et al., "Intelligent Widgets for Intuitive Interaction and Coordination in Smart Home Environments," IEEE Eighth International Conference on Intelligent Environments, pp. 157-164, 2012.
Wu et al., "A Web 2.0 Based Scientific Application Framework," 7 pages, prior to Jul. 24, 2014.
"4.0 Today's Activities, The Home Dashboard," CRBM info@hand website, 46 pages, prior to Apr. 25, 2013.
"Free Facilities Dashboards," eSight Energy Website, 2 pages, prior to Apr. 25, 2013.
Alerton Building Controls, Gallery Prints, 7 pages, Dec. 19, 2013.
Carter, "Industrial Energy Management Dashboards Require a Toolkit," Cross Automation, 11 pages, Nov. 4, 2013.
U.S. Appl. No. 14/169,071, filed Jan. 30, 2014.
U.S. Appl. No. 14/169,083, filed Jan. 30, 2014.
U.S. Appl. No. 14/461,188, filed Aug. 15, 2014.
U.S. Appl. No. 14/482,607, filed Sep. 10, 2014.
e-homecontrols.com, "e-Home Controls Website," link to actual website no longer works, 1 page, prior to Dec. 19, 2013.
http://www.ccbac.com, "C&C (/)—Omniboard," 5 pages, Dec. 19, 2013.
http://www.domcontroller.com/en/, "DomController Home Automation Software—Control Anything from Anywhere," 11 pages, printed Jan. 6, 2015.
http://www.novar.com/ems-bas/opus-building-automation-system, "Novar Opus Bas," 1 page, prior to Feb. 13, 2013.
Instituto Superior Tecnico, "A 3D Interactive Environment for Automated Building Control," Master's Dissertation, 120 pages, Nov. 2012.
Panduit Corp., "Enable a Building Automation with Panduit Enterprise Solutions," 4 pages, Nov. 2012.
"WEBs-AX Web-Enabled Building Solutions," sales brochure, Honeywell International Inc., Mar. 2009.
"Attune Advisory Services," press release, Honeywell International Inc., Mar. 20, 2012.
EnteliWEB product from Delta Controls, web pages retrieved on May 9, 2013 from http://deltacontrols.com/products/facilities-management/supervisory-software et seq. by the Internet Archive at web archive.org.
"BACnet Protocol Implementation Conformance Statement" for enteliWEB, Delta Controls, Jul. 17, 2013.
Castle, "7 Software Platforms that Make Building Energy Management Easy," http://greentechadvocates.com/2012/11/28/7-software-platforms-that-make-building-energy-managment-easy/, Nov. 28, 2012.
EnteliWEB catalog sheet, Delta Controls, Inc., 2012.
EnteliWEB catalog sheet, Delta Controls., 2010.
"Intelligent Building Management Systems in Miami," Advanced Control Corp., Mar. 7, 2013.
"The Ohio State University," BACnet International Journal, vol. 5, p. 4, Jan. 2013.
Bobker et al., "Operational Effectiveness in Use of BAS," Proceedings of the 13th International Conference for Enhanced Building Operations, Oct. 8, 2013.
Castelo, "A 3D Interactive Environment for Automated Building Control," Elsevier, Nov. 8, 2012.
"Creston Special Report: How Intelligent building management solutions are reducing operational costs," Creston, 2012.
"Building Automation Software Solutions," Iconics, 2013.
Lacey, "The Top 10 Software Vendors Connecting Smart Buildings to the Smart Grid," http://www.greentechmedia.com/articles/read/the-top-10-companies-in-enterprise-smart-grid, Jul. 18, 2013.
"NiagraAX Product Model Overview," Tridium, Inc., 2005.
"An Overview of NiagraAX: A comprehensive software platform designed to create smart device applications," Tridium, Inc., 2005.
"Phoenix Controls Portal," Phoenix Controls, Inc., 2013.
Quirk, "A Brief History of BIM," Arch Daily, Dec. 7, 2012.
Samad et al., "Leveraging the Web: A Universal Framework for Building Automation," Proceedings of the 2007 American Control Conference, Jul. 11, 2007.
Sinha et al., "9 Key attributes of energy dashboards and analytics tools," https://www.greenbiz.com/blog/2013/08/28/9-key-attributes-energy-dashboards-and=analytics-tools, Aug. 28, 2013.
Sinopoli, "Dashboards For Buildings," http://www/automatedbuildings.com/news/dec10/articles/sinopoli/101119034404sinopoli.html, Dec. 2010.
Sinopoli, "Modeling Building Automation and Control Systems," http://www.automatedbuildings.com/news/jun13/articles/sinopoli/130521122303sinopoli.html, Jun. 2013.
Zito, "What is Tridium Part 1," http://blog.buildingautomationmonthly.com/what-is-tridium/, May 12, 2013.
Zito, "What is Tridium Part 2," http://blog.buildingautomationmonthly.com/tridium-part-2/, Sep. 10, 2013.
Search Report and Written Opinion from related International PCT Application No. PCT/US2018/025189 dated Jul. 17, 2018 (12 pages).
"Data analytics and smart buildings increase comfort and energy efficiency", https://www.microsoft.com/itshowcase/Article/Content/845/Data-analytics-and-smart-buildings-increase-comfort-and-energy-efficiency, Dec. 19, 2016, 8 pages.
Donnelly, "Building Energy Management: Using Data as a Tool", http://www.buildingefficiencyinitiative.org/sites/default/files/legacy/InstituteBE/media/Library/Resources/Existing-Building-Retrofits/Using-Building-Data-as-a-Tool.pdf, Oct. 2012, 9 pages.
"Ashrae Dashboard Research Project," 29 pages, Aug. 28, 2008.
Shhedi, Zaid Ali, et al., "Traditional & ICT Solutions for preventing the Hospital Acquired Infection," 2015 20th International Confer-

(56) References Cited

OTHER PUBLICATIONS ence on Control Systems and Science, IEEE, May 27, 2015, pp. 867-873, XP933188038, DOI: 10.1109/CSCS.2015.125.

Bocicor, I., et al., "Wireless Sensor Network based System for the Prevention of Hospital Acquired Infections," arxiv.org, Cornell University Library, 201 Olin Library Cornell University Ithaca, NY 14853, May 2, 2017, XP080947042.

EP Communication pursuant to Article 94(3) EPC, European Patent Office, EP Application No. 20 151 295.1, dated Mar. 29, 2023 (9 pages).

* cited by examiner

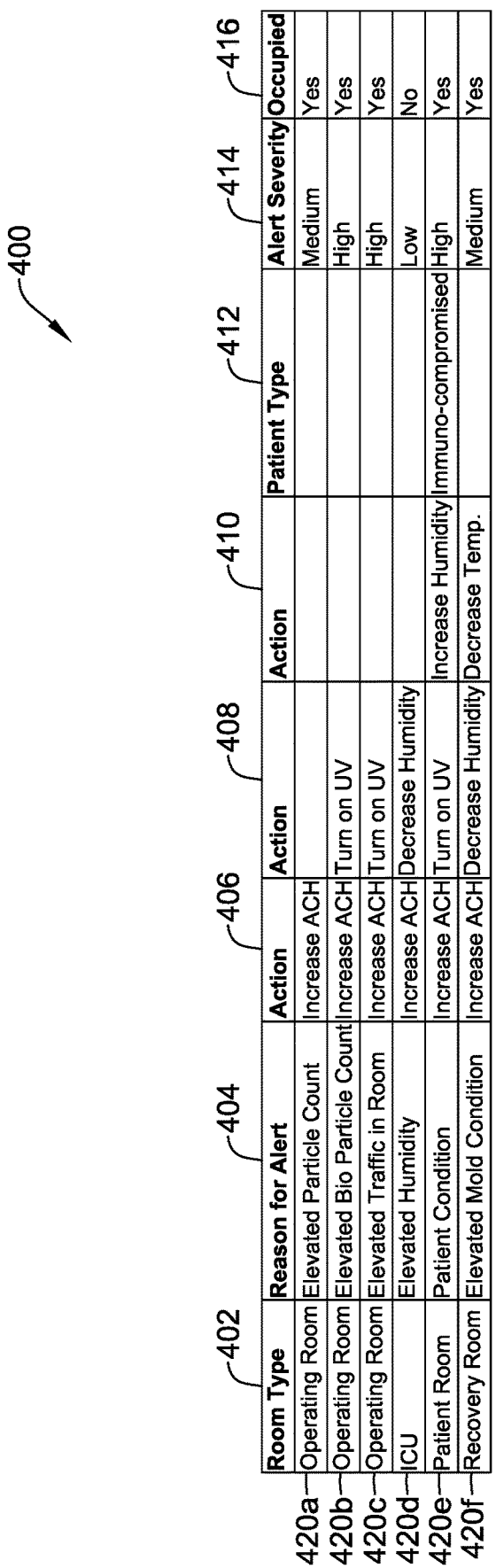

| | Room Type | Reason for Alert | Action | Action | Action | Action | Patient Type | Alert Severity | Occupied |
|---|---|---|---|---|---|---|---|---|---|
| 420a | Operating Room | Elevated Particle Count | Increase ACH | | | | | Medium | Yes |
| 420b | Operating Room | Elevated Bio Particle Count | Increase ACH | Turn on UV | | | | High | Yes |
| 420c | Operating Room | Elevated Traffic in Room | Increase ACH | Turn on UV | | | | High | Yes |
| 420d | ICU | Elevated Humidity | Increase ACH | Decrease Humidity | | | | Low | No |
| 420e | Patient Room | Patient Condition | Increase ACH | Turn on UV | Increase Humidity | | Immuno-compromised | High | Yes |
| 420f | Recovery Room | Elevated Mold Condition | Increase ACH | Decrease Humidity | Decrease Temp. | | | Medium | Yes |

FIG. 5

METHODS AND SYSTEMS FOR IMPROVING INFECTION CONTROL IN A BUILDING

This is a continuation of co-pending U.S. patent application Ser. No. 16/246,437, filed Jan. 11, 2019, and entitled "METHODS AND SYSTEMS FOR IMPROVING INFECTION CONTROL IN A BUILDING", which is incorporated herein by reference.

TECHNICAL FIELD

The disclosure generally relates to building management systems, and more particularly to systems and methods for monitoring and manipulating conditions in a building to reduce the risk of infection for building occupants.

BACKGROUND

Hospital Acquired Infections (HAI) and/or Surgical Staff Infections (SSI) are infections caused by virus, bacteria and other environmental factors and are acquired within hospitals or other medical treatment facilities. It is estimated that HAI and SSI infections cost the healthcare industry nearly $40 billion annually. HAI and SSI infections can be transmitted in multiple ways, including, but not limited to, surface contamination, airborne particulates and aspiration. Depending on the medical application, activity, surgical procedure, and/or susceptibility of the patient, it is believed that airborne particulates may contribute up to 90% of the HAI or SSI cases. Room contamination from outside air, such as from door openings in an operating room, were also found to directly correlated to increased HAI and SSI.

What would be desirable is a building management system (BMS) that is configured to improve healthcare hygiene and/or indoor environmental conditions within a building to help reduce HAI and SSI.

SUMMARY

This disclosure generally relates to systems and methods for reducing a risk of infection in a medical facility.

In a first example, a method for controlling a building management system of a medical facility including a plurality of rooms with at least one of the rooms having a plurality of sensors, wherein an elevated infection risk determination system is operative coupled to the plurality of sensors for determining an elevated infection risk in one or more of the rooms of the medical facility may comprise receiving one or more programmable infection risk compliance parameters for a particular room in the medical facility and storing the received one or more programmable infection risk compliance parameters in a memory. The method may further comprise receiving from the elevated infection risk determination system an elevated infection risk alert for the particular room in the medical facility and in response to receiving the elevated infection risk alert for the particular room, controlling the building management system in accordance with the one or more programmable infection risk compliance parameters for the particular room to help mitigate the elevated infection risk in the particular room.

In another example, a building management system (BMS) for a medical facility that includes a plurality of rooms with at least one of the rooms having a plurality of sensors, wherein an elevated infection risk determination system is operatively coupled to the plurality of sensors for determining an elevated infection risk in one or more of the rooms of the medical facility may comprise a memory for storing one or more programmable infection risk compliance parameters for a particular room in the medical facility, an input port for receiving from the elevated infection risk determination system an elevated infection risk alert for the particular room in the medical facility, a control port for providing control commands to one or more building components of the building management system, and a controller operatively coupled to the memory, the input port and the control port. The controller may be configured to provide control commands via the control port in response to receiving the elevated infection risk alert for the particular room to help mitigate the elevated infection risk in the particular room, wherein the one or more control commands control the building management system in accordance with the one or more programmable infection risk compliance parameters for the particular room.

In another example, a method for controlling a building management system of a medical facility, wherein the medical facility includes a plurality of rooms of different room types, with at least one of the rooms having a plurality of sensors, wherein an elevated infection risk determination system is operative coupled to the plurality of sensors for determining an elevated infection risk in one or more of the rooms of the medical facility may comprise receiving one or more programmable infection risk compliance parameters for each of the different room types, receiving from the elevated infection risk determination system an elevated infection risk alert for a particular room in the medical facility having a particular room type, and in response to receiving the elevated infection risk alert for the particular room that has a particular room type, controlling the building management system in accordance with the one or more programmable infection risk compliance parameters that correspond to the particular room type to help mitigate the elevated infection risk in the particular room.

The preceding summary is provided to facilitate an understanding of some of the features of the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following detailed description of various embodiments in connection with the accompanying drawings, in which:

FIG. 5 shows database entries of illustrative programmable infection risk compliance parameters.

Figure 1:
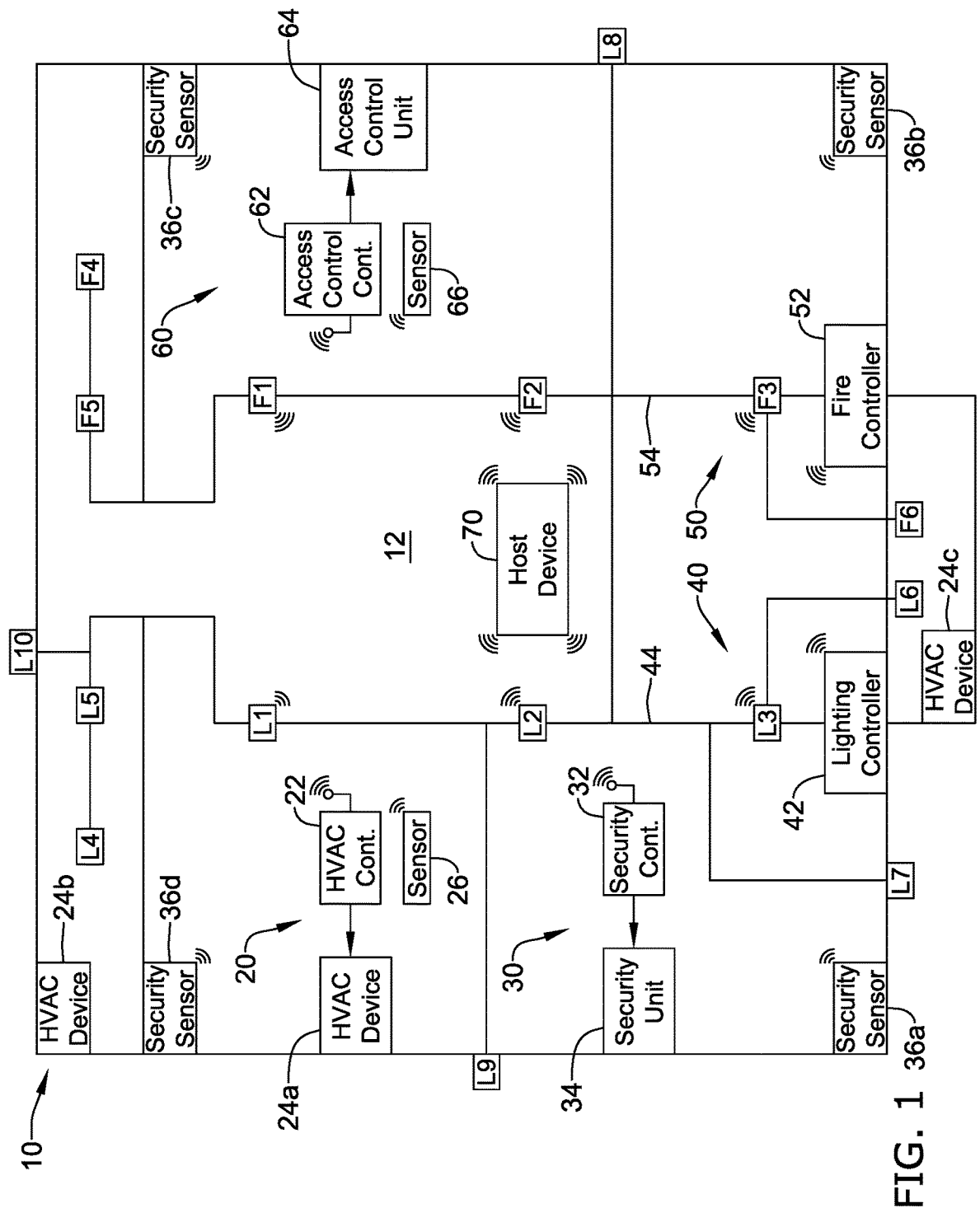
FIG. 1 is a schematic view of a building or other structure that includes an illustrative building management system (BMS) that controls client devices servicing the building or other structure.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DESCRIPTION

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure generally relates to building management systems, and more particularly to systems and methods for monitoring and manipulating conditions in a building to help reduce the risk of infection for building occupants. FIG. 1 is a schematic view of a building or structure 10 that includes an illustrative building management system (BMS) 12 for controlling one or more client devices servicing the building or structure 10. The BMS 12, as described herein according to the various illustrative embodiments, may be used to control the one or more client devices in order to control certain environmental conditions (e.g., temperature, ventilation, humidity, lighting, etc.) to reduce the risk of infection for building occupants. While such a BMS 12 may be implemented in a hospital or other clinical setting, it contemplated that the BMS 12 may be included in other buildings such as office buildings, health clubs, movie theaters, restaurants, and even residential homes.

The illustrative BMS 12 shown in FIG. 1 includes one or more heating, ventilation, and air conditioning (HVAC) systems 20, one or more security systems 30, one or more lighting systems 40, one or more fire systems 50, and one or more access control systems 60. These are just a few examples of systems that may be included or controlled by the BMS 12. In some cases, the BMS 12 may include more or fewer systems. In some cases, each system may include a client device configured to provide one or more control signals for controlling one or more building control components and/or devices of the BMS 12.

For instance, in some cases, the HVAC system 20 may include an HVAC control device 22 used to communicate with and control one or more HVAC devices 24a, 24b, and 24c (collectively, 24) for servicing the HVAC needs of the building or structure 10. While the HVAC system 20 is illustrated as including three devices, it should be understood that the structure may include fewer than three or more than three devices 24, as desired. Some illustrative devices may include, but are not limited to a furnace, a heat pump, an electric heat pump, a geothermal heat pump, an electric heating unit, an air conditioning unit, a humidifier, a dehumidifier, an air exchanger, an air cleaner, a damper, a valve, blowers, fans, motors, and/or the like. The HVAC system 20 may further include a system of ductwork and air vents (not explicitly shown). The HVAC system 20 may further include one or more sensors or devices 26 configured to measure parameters of the environment to be controlled. The HVAC system 20 may include more than one sensor or device of each type, as needed to control the system. It is contemplated that large buildings, such as, but not limited to, a hospital, may include a plurality of different sensors in each room or within certain types of rooms. The one or more sensors or devices 26 may include, but are not limited to, temperatures sensors, humidity sensors, carbon dioxide sensors, occupancy sensors, proximity sensors, etc. Each of the sensor/devices 26 may be operatively connected to the controller 22 via a corresponding communications port (not explicitly shown). It is contemplated that the communications port may be wired and/or wireless. When the communications port is wireless, the communications port may include a wireless transceiver, and the controller 22 may include a compatible wireless transceiver. It is contemplated that the wireless transceivers may communicate using a standard and/or a proprietary communication protocol. Suitable standard wireless protocols may include, for example, cellular communication, ZigBee, Bluetooth, WiFi, IrDA, dedicated short range communication (DSRC), EnOcean, or any other suitable wireless protocols, as desired.

In some cases, the security system 30 may include a security control device 32 used to communicate with and control one or more security units 34 for monitoring the building or structure 10. The security system 30 may further include a number of sensors/devices 36a, 36b, 36c, 36d (collectively, 36). The sensor/devices 36 may be configured to detect threats within and/or around the building 10. In some cases, some of the sensor/devices 36 may be constructed to detect different threats. For example, some of the sensor/devices 36 may be limit switches located on doors and windows of the building 10, which are activated by entry of an intruder into the building 10 through the doors and windows. Other suitable security sensor/devices 12 may include fire, smoke, water, carbon monoxide, and/or natural gas detectors, to name a few. Still other suitable security system sensor/devices 36 may include motion sensors that detect motion of intruders in the building 10, noise sensors or microphones that detect the sound of breaking glass, security card pass systems, or electronic locks, etc. It is contemplated that the motion sensor may be passive infrared (PIR) motion sensors, a microwave motion sensor, an ultrasonic motion sensor, a tomographic motion sensor, a video camera having motion detection software, a vibrational motion sensor, etc. In some cases, one or more of the sensor/devices 36 may include a video camera. In some cases, the sensor/devices 36 may include a horn or alarm, a damper actuator controller (e.g. that closes a damper during a fire event), a light controller for automatically turning on/off lights to simulate occupancy, and/or any other suitable device/sensor. These are just examples.

In some cases, the lighting system 40 may include a lighting control device 42 used to communicate with and control one or more light banks 44 having lighting units L1-L10 for servicing the building or structure 10. In some embodiments, one or more of the lighting units L1-L10 may be configured to provide visual illumination (e.g., in the visible spectrum) and one or more of the light units L1-L10 may be configured to provide ultraviolet (UV) light to provide irradiation. The lighting system 40 may include emergency lights, outlets, lighting, exterior lights, drapes, and general load switching, some of which are subject to "dimming" control which varies the amount of power delivered to the various building control devices.

In some cases, the fire system 50 may include a fire control device 52 used to communicate with and control one or more fire banks 54 having fire units F1-F6 for monitoring and servicing the building or structure 10. The fire system 50 may include smoke/heat sensors, a sprinkler system, warning lights, and so forth. In some cases, the access control system 60 may include an access control device 62 used to communicate with and control one or more access control units 64 for allowing access in, out, and/or around the building or structure 10. The access control system 60 may include doors, door locks, windows, window locks, turnstiles, parking gates, elevators, or other physical barrier, where granting access can be electronically controlled. In some embodiments, the access control system 60 may include one or more sensors 66 (e.g., RFID, etc.) configured to allow access to the building or certain parts of the building 10.

In a simplified example, the BMS 12 may be used to control a single HVAC system 20, a single security system 30, a single lighting system 40, a single fire system 50, and/or a single access control system 60. In other embodiments, the BMS 12 may be used to communicate with and control multiple discrete building control devices 22, 32, 42, 52, and 62 of multiple systems 20, 30, 40, 50, 60. The devices, units, and controllers of the systems 20, 30, 40, 50, 60 may be located in different zones and rooms, such as a common space area (a lobby, a waiting room, etc.), in a dedicated space (e.g., a patient room, an operating room, etc.) or outside of the building 10. In some cases, the systems 20, 30, 40, 50, 60 may be powered by line voltage, and may be powered by the same or different electrical circuit. It is contemplated that the BMS 12 may be used to control other suitable building control components that may be used to service the building or structure 10.

According to various embodiments, the BMS 12 may include a host device 70 that may be configured to communicate with the discrete systems 20, 30, 40, 50, 60 of the BMS 12. In some cases, the host device 70 may be configured with an application program that assigns devices of the discrete systems to a particular device (entity) class (e.g., common space device, dedicated space device, outdoor lighting, unitary controller, and so on). In some cases, there may be multiple hosts. For instance, in some examples, the host device 70 may be one or many of the control devices 22, 32, 42, 52, 62.

In some cases, the building control devices 22, 32, 42, 52, 62 may be configured to transmit a command signal to its corresponding building control component(s) for activating or deactivating the building control component(s) in a desired manner. In some cases, the building control devices 22, 32, 42, 52, 62 may be configured to receive a classification of building control component and may transmit a corresponding command signals to their respective building control component in consideration of the classification of the building control component.

In some instances, the building control devices 22, 32, 62 may be configured to receive signals from one or more sensors 26, 36, 66 located throughout the building or structure 10. In some cases, the building control devices 42 and 52 may be configured to receive signals from one or more sensors operatively and/or communicatively coupled with the lighting units L1-L10 and the fire units F1-F6 located throughout the building or structure 10, respectively. In some cases, the one or more sensors may be integrated with and form a part of one or more of their respective building control devices 22, 32, 42, 52, 62. In other cases, one or more sensors may be provided as separate components from the corresponding building control device. In still other instances, some sensors may be separate components of their corresponding building control devices while others may be integrated with their corresponding building control device. These are just some examples. The building control devices 22, 32, 42, 52, 62 and the host device 70 may be configured to use signal(s) received from the one or more sensors to operate or coordinate operation of the various BMS systems 20, 30, 40, 50, 60 located throughout the building or structure 10.

The one or more sensors 26, 36, 66, L1-L10, and F1-F6 may be any one of a temperature sensor, a humidity sensor, an occupancy sensor, a light sensor, a video camera, a current sensor, a smoke sensor and/or any other suitable sensor. In one example, at least one of the sensors 26, 36, 66, or other sensors, may be an occupancy sensor. The building control devices 22, 32, 42, 62 and/or the host device 70 may receive a signal from the occupancy sensor indicative of occupancy within a room or zone of the building or structure 10. In response, the building control devices 22, 32, 42, and/or 62 may send a command to activate one or more building control component(s) located in or servicing the room or zone where occupancy is sensed.

Likewise, in some cases, at least one of the sensors 26 may be a temperature sensor configured to send a signal indicative of the current temperature in a room or zone of the building or structure 10. The building control device 22 may receive the signal indicative of the current temperature from the temperature sensor 26. In response, the building control device 22 may send a command to an HVAC device 24 to activate and/or deactivate the HVAC device 24 that is in or is servicing that room or zone to regulate the temperature in accordance with a desired temperature set point.

In yet another example, one or more of the sensors may be a current sensor. The current sensor may be coupled to the one or more building control components and/or an electrical circuit providing electrical power to one or more building control components. The current sensors may be configured to send a signal to a corresponding building control device, which indicates an increase or decrease in electrical current associated with the operation of the building control component. This signal may be used to provide confirmation that a command transmitted by a building control device has been successfully received and acted upon by the building control component(s). These are just a few examples of the configuration of the BMS 12 and the communication that can take place between the sensors and the control devices.

Figure 2:
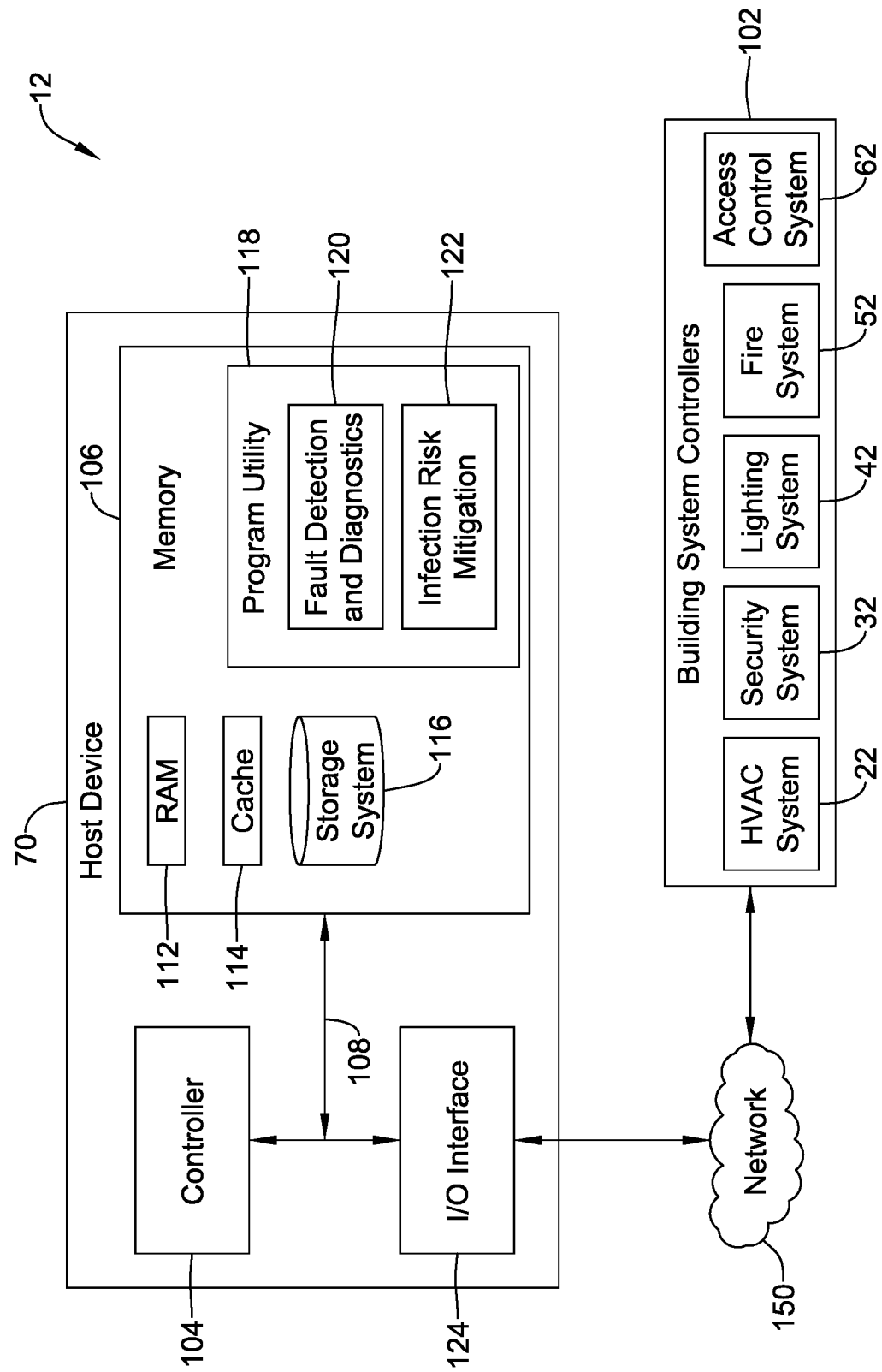
FIG. 2 is a schematic block diagram of the illustrative BMS of FIG. 1.

As shown in FIG. 2, the host device 70 can function as a server, a client, a local controller, or any other suitable device. In the example shown, the host device 70 can perform various communication and data transfer functions as described herein and can execute one or more application functions. The host device 70 can be any of a variety of computing devices, such as a server computer, a desktop computer, a handheld computer, a tablet computer, mobile telephone or other mobile device, and the like. The components of the host device 70 may include, but are not limited to, a controller 104, a system memory 106, and a bus 108 that couples various system components including the system memory 106 to the controller 104.

The controller 104 may include one or more controllers or processors that execute instructions stored in the system memory 106. The controller 104 may include a programmable microprocessor. Such a programmable microprocessor may allow a user to modify the control logic of the host device 70 even after it is installed in the field (e.g., firmware update, application update). When provided, the bus 108 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA)

bus, Video Electronics Standards Association (VESA) local bus, and Peripheral Component Interconnect (PCI) bus.

The system memory 106 of the host device 70 can include computer system readable media in the form of volatile memory, such as random access memory (RAM) 112 and/or cache memory 114. The host device 70 may further include other removable/non-removable, volatile/non-volatile computer system storage media. By way of example only, the storage system 116 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 108 by one or more data media interfaces. As will be further depicted and described below, the system memory 106 may include at least one program/utility 118 having a set of program modules that are configured to receive an input from an infection risk determination system and control (or send control commands) to at least a portion of the BMS to mitigate an elevated infection risk.

In one example, the program/utility 118 may be stored in the system memory 106 and may include one or more application program modules (e.g., software), such as fault detection and diagnostics (FDD) module 120 and/or infection risk mitigation module 122. In some cases, the program/utility 118 may include additional program modules as well as an operating system, one or more other application program modules, and program data. The FDD module 120 and/or infection risk mitigation module 122 may execute on the host device 70. In some cases, the FDD module 120 and/or infection risk mitigation module 122 may execute on one or many of the building system controllers 102. In some cases, part of the FDD module 120 and/or infection risk mitigation module 122 is executed on the host device 70 and part of the FDD module 120 and/or infection risk mitigation module 122 is executed on the building system controllers 102. In any scenario, the building system controllers 102 may be connected to the host device 70 through any type of connection such as a network (e.g., network 150), including a local area network (LAN) or a wide area network (WAN), or the connection may be made to an external computer (for example, through the Internet using an Internet Service Provider). In various embodiments, the host device 70 may communicate with one or more devices from the various systems of the building system controllers 102 over the network 150. Such communication can occur via Input/Output (I/O) interface(s) 124. In some cases, the controller 104 of the host device 70 may be operatively coupled to I/O interface(s) 124 via the bus 108, and may use the I/O interface 124 to communicate with devices via the building system controllers 102.

Figure 3:
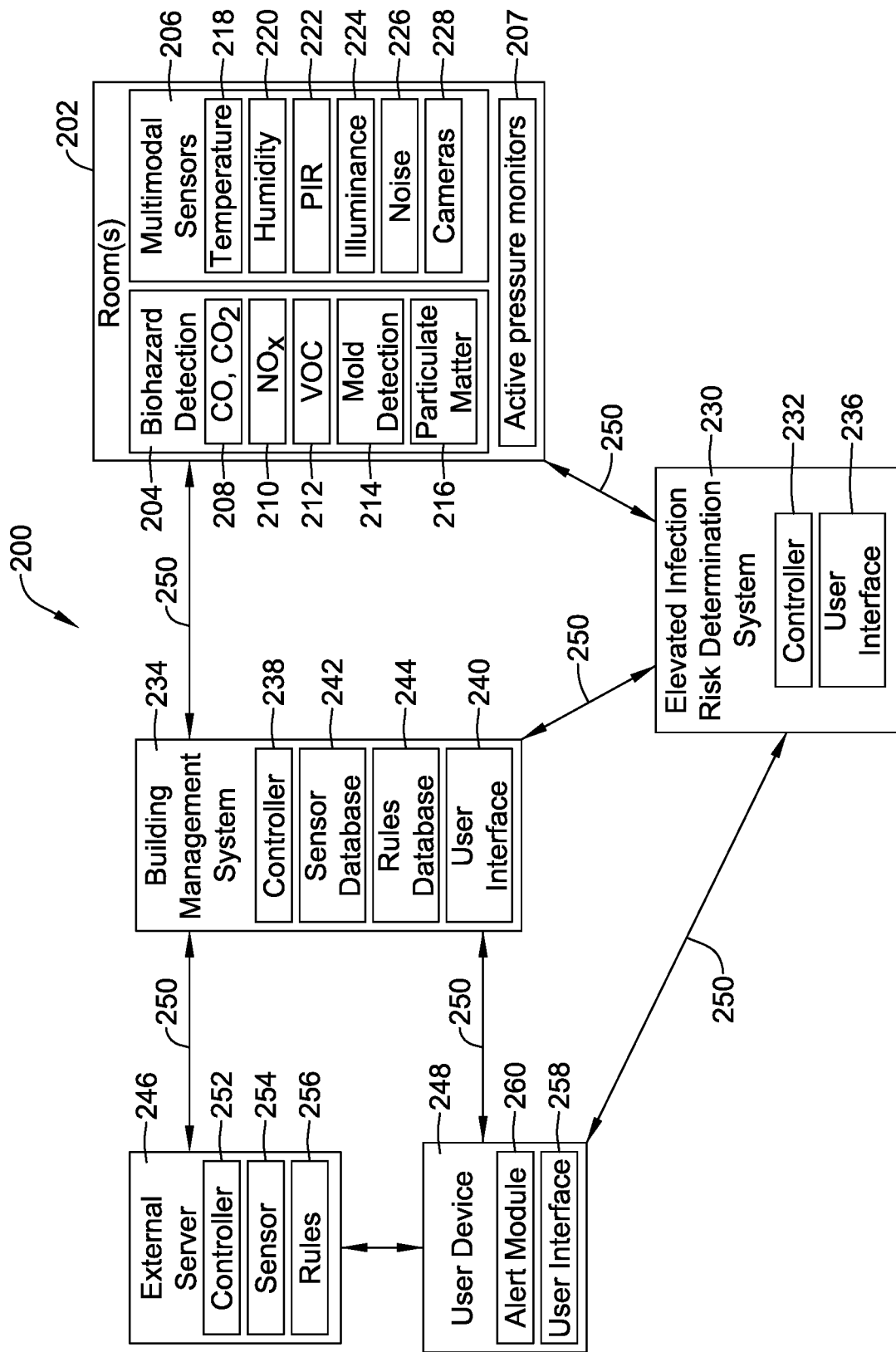
FIG. 3 is a schematic block diagram of an illustrative infection risk reduction system that uses a building management system (BMS)

FIG. 3 is a schematic block diagram of an illustrative infection risk reduction system that uses a building management system (BMS) 234. While the BMS 234 is described with respect to a medical facility, it is contemplated that the BMS may service another type of building, such as, but not limited to those described above with respect to FIG. 1. In the example shown, the medical facility may include a plurality of rooms 202 with at least one room of the plurality of rooms including a plurality of sensors. In some cases, more than one room may be provided, each with a plurality of sensors. For example, if a medical facility has three operating rooms, each operating room may have one or more sensors configured to monitor the conditions in the room in which they are located. It is contemplated that other room types may have sensors as well, such an intensive care unit (ICU), patient recovery rooms, etc. Further, different types of sensors or sensor combinations may be provided within the rooms depending on the type of room, the procedures performed in the room, patient privacy expectations in the room, etc. The sensors may include, but are not limited to biohazard detection sensors 204, multimodal sensors 206, and/or active pressure monitors (APM) 207. Some illustrative biohazard detection sensors 204 may include, but are not limited to, carbon monoxide (CO) and/or carbon dioxide ($CO_2$) sensors 208, NOx (oxides of nitrogen) sensors 210, volatile organic chemical (VOC) sensors 212 (e.g., formaldehyde sensors), mold detectors 214, particulate matter (PM) sensors 216, etc. Some illustrative multimodal sensors 206 may include, but are not limited to, temperature sensors 218, humidity sensors 220, passive infrared (PIR) sensors 222, illuminance sensors 224, noise sensors 226, cameras 228, etc. Other sensors may include limit switches and door sensors.

The room(s) 202 and/or sensors 204, 206, 207 may be in communication with an elevated risk determination system 230 over one or more networks 250, such as a local area network (LAN) and/or a wide area network or global network (WAN) including, for example, the Internet. In some embodiments, some portions of the infection risk reduction system 200 may be in communication over a LAN while other portions of the infection risk reduction system 200 may communicate over a WAN. Some portions of the infection risk reduction system 200 may be configured to communicate over both a LAN and a WAN. The elevated risk determination system 230 may include a controller 232 configured to receive data from the one or more sensors 204, 206, 207 and determine if conditions are present that are indicative of an increased likelihood (e.g., an increased risk or chance) that a patient in the room(s) 202 will acquire an infection. The elevated risk determination system 230 may be configured to transmit an alert, such as, but not limited to an elevated infection risk for a particular room in the medical facility to the BMS 234. In some cases, the elevated infection risk alert may be a binary alert, such as a flag that is raised when the risk of infection crosses a threshold. In other cases, the elevated infection risk alert may present the risk along a scale of risk, from low to high. In some cases, the elevated infection risk alert may include additional information such as what sensed conditions caused or formed the basis of the elevated infection risk alert. It is contemplated that the location of the sensor 204, 206, 207 that triggered the alert may be included in and/or accessible from the sensor database 242 of the building management system 234.

The controller 232 may include at least a processor and a memory for storing information, such as, but not limited to risk analysis rules, sensor location information, set points, diagnostic limits, medical procedure information, surgical tool location, etc. The memory may be any suitable type of storage device including, but not limited to, RAM, ROM, EPROM, flash memory, a hard drive, and/or the like. In some cases, the processor may store information within the memory and may subsequently retrieve the stored information from the memory. The controller 232 may further include an input/output block (I/O block) for receiving one or more signals from the sensors 204, 206, 207 and/or for communicating with the building management system 234. The I/O block may be wired and/or wireless.

In some embodiments, the elevated risk determination system 230 may include a user interface 236 that permits the elevated risk determination system 230 to display and/or solicit information, as well as accept one or more user interactions. In one example, the user interface 236 may be a physical user interface that is accessible at the elevated risk determination system 230, and may include a display and/or a distinct keypad. The display may be any suitable display. In some instances, a display may include or may be a liquid crystal display (LCD), and in some cases an e-ink display, fixed segment display, or a dot matrix LCD display. In other cases, the user interface 236 may be a touch screen LCD panel that functions as both display and keypad. The touch screen LCD panel may be adapted to solicit values for a number of operating parameters and/or to receive such values, but this is not required. In still other cases, the user interface 236 may be a dynamic graphical user interface.

In some instances, the user interface 236 need not be physically accessible to a user at the elevated risk determination system 230. Instead, the user interface 236 may be a virtual user interface 236 that is accessible via the network 250 using a mobile wireless device 248 such as a smart phone, tablet, e-reader, laptop computer, personal computer, key fob, or the like. In some cases, the virtual user interface 236 may be provided by an app or apps executed by a user's remote device for the purposes of remotely interacting with the elevated risk determination system 230 controller 232.

The room(s) 202 and/or sensors 204, 206, 207 may be in communication with the building management system 234 over the one or more networks 250. The building management system 234 may include a controller 238 configured to receive data from the one or more sensors 204, 206, 207. The illustrative building management system 234 includes a controller 238. In some embodiments, the controller 238 may be a host controller, such as the host device 70 described with respect to FIGS. 1 and 2. In other embodiments, the controller 238 may be a system controller, such as any of the system controllers described herein. For example, the controller 238 may include at least a processor and a memory for storing information, such as, but not limited to rules, set points, diagnostic limits, medical procedure information, compliance parameters, clinical parameters, etc.

The memory may be any suitable type of storage device including, but not limited to, RAM, ROM, EPROM, flash memory, a hard drive, and/or the like. In some cases, the processor may store information within the memory and may subsequently retrieve the stored information from the memory. The controller 238 may further include an input/output block (I/O block) for receiving one or more signals from the sensors 204, 206, 207 and/or the elevated risk determination system 230. The I/O block may be configured to receive wired or wireless signals. It is further contemplated that the controller 238 may further include a control port for providing control commands to one or more building components of the building management system 234. In some cases, the control commands may be in response to receiving the elevated infection risk alert for a particular room and may be tailored to help mitigate the elevated infection risk in that particular room. The one or more control commands may control the building management system in accordance with one or more programmable infection risk compliance parameters for the particular room, as will be described in more detail herein.

In some embodiments, the building management system 234 may include a user interface 240 that permits the building management system 234 to display and/or solicit information, as well as accept one or more user interactions. In one example, the user interface 240 may be a physical user interface that is accessible at the building management system 234, and may include a display and/or a distinct keypad. The display may be any suitable display. In some instances, a display may include or may be a liquid crystal display (LCD), and in some cases an e-ink display, fixed segment display, or a dot matrix LCD display. In other cases, the user interface 240 may be a touch screen LCD panel that functions as both display and keypad. The touch screen LCD panel may be adapted to solicit values for a number of operating parameters and/or to receive such values, but this is not required. In still other cases, the user interface 240 may be a dynamic graphical user interface.

In some instances, the user interface 240 need not be physically accessible to a user at the building management system 234. Instead, the user interface 240 may be a virtual user interface 240 that is accessible via the network 250 using a mobile wireless device such as a smart phone, tablet, e-reader, laptop computer, personal computer, key fob, or the like. In some cases, the virtual user interface 240 may be provided by an app or apps executed by a user's remote device for the purposes of remotely interacting with the building management system 234 controller 238.

The building management system 234 may maintain a first, or sensor, database 242 of data obtained from the one or more sensors 204, 206, 207. For example, a memory accessible by the processor of the controller 238 may be configured to store the database 242 of sensor data such that historical and current sensor data is readily accessible. In some cases, the building management system 234 may only have access to the multimodal sensors 206 and thus the database 242 of sensor data may only store data for these sensors. The building management system(s) 234 may maintain a second, or rules, database 244 that includes a set of rules or algorithms that may be used to identify actions that should be taken to lower a patient's risk of infection. In some cases, the rules database 244 may also include one or more programmable infection risk compliance parameters. In some cases, the rules or algorithms may be used to control the building management system 234 in accordance with one or more programmable risk compliance parameters for a particular room to help mitigate the elevated infection risk in the particular room. A set of rules may include at least one rule, two or more rules, three or more rules, etc. The elevated infection risk alert may be received from the elevated risk determination system 230 and is based on the detected conditions (e.g., from the sensors 204, 206, 207) in a particular room. The set of rules may determine what action to take to reduce the elevated infection risk, sometimes in accordance with the one or more programmable risk compliance parameters for the particular room. A memory accessible by the processor of the controller 238 may be configured to store the rules database 242 and/or the one or more programmable risk compliance parameters for each room, such that the rules and algorithms are readily accessible.

The rules database 244 may be downloaded onto the controller 238 of the building management system 234 from an external server(s) 246 over a network 250, although this is not required. The network 250 may be a wide area network or global network (WAN), such as the internet. The external server(s) 246 may be a suite of hardware and software which may sometimes be referred to as "the cloud." In some cases, the communication may pass through an intermediary server or cloud network, but this is not required. In some cases, the cloud may provide the ability for communication amongst the building management system 234, the elevated risk determination system 230, the external server(s) 246, and/or one or more remote devices 248. While the external server(s) 246 is illustrated as connected to a building management system 234, the external server(s) 246 may be connected to a plurality of building management systems. The external server(s) 246 may collect and store sensor data 254 from the various sensors 204, 206, 207 from the one or more connected building management systems 234. The external server(s) 246 may include a controller 252 configured to analyze the sensor data and determine if the rules stored in a network rules database 256 need to be or could be improved by updating the rules from time to time.

Returning to the elevated risk determination system 230, the data from the sensors 204, 206, 207 may be analyzed for conditions that increase a risk of infection to a patient. Some conditions that may increase a risk of infection include, but are not limited to, a high particulate count, a high humidity level, a low humidity level, a high room temperature, high traffic into, out of, and/or within the room, high biological particle levels, low air changes per hour (ACH), low air velocity, high air velocity, high mold conditions, etc. These are just some examples of conditions which may impact a risk of infection. While the terms "high" and "low" are relative terms, it should be understood that as used herein, high is to be interpreted as exceeding or above a predetermined threshold while low is to be interpreted as under or below a predetermined threshold. The predetermined threshold may be user defined, defined by one or more programmable risk compliance parameters, or a combination thereof.

When the elevated risk determination system 230 detects a condition that is indicative of an elevated risk of infection in a particular room 202 of the one or more rooms, the elevated risk determination system 230 transmits an alert or signal to the building management system 234. In some cases, the elevated infection risk alert may include additional information such as what sensed conditions caused or formed the basis of the elevated infection risk alert. In response, the controller 238 of the building management system 234 may apply appropriate rules in the rules database 244, and the applied rules may inform the controller 238 how to control the building management system 234 in that particular room. This may include changing one or more control parameters of the building management system 234 as dictated by the one or more rules that correspond to elevated infection risk alert. It is contemplated that a change in the control of the building management system 234 or change in control parameter of the building management system 234 may vary depending on the particular room that resulted in the elevated infection risk alert (e.g., an operating room, a general patient room, a waiting room, etc.), a condition of a patient or patients in the particular room, (e.g., respiration issues, germ shedding, open wound, broken bone, etc.) a degree of severity of the elevated infection risk alert if provided, etc. These are just some examples of factors that may be considered by the rules when defining an action to take in response to an elevated infection risk alert. It is contemplated that some scenarios may require a more conservative control or change to the building management system 234 while other conditions may require more severe changes in the control of the building management system 234.

In some cases, the processing of the sensor data may be performed in the cloud or remote from the controller 232 of the elevated risk determination system 230, although this is not required. In some embodiments, an elevated infection risk alert may be sent to a remote device 248 by the elevated risk determination system 230. The remote device 248 may be any internet connected device including a smart phone, tablet, e-reader, laptop computer, personal computer, etc. The notification may be received by an application program code (app) or other module 260 within the remote device 248. Once the notification has been received at the notification module 260, the notification may be displayed on the user interface 2586 of the device 248. In some cases, an audio alert (e.g., a beep or chime) or a haptic alert (e.g., a vibration) may accompany the notification.

It is contemplated that the rules database 244 may be tailored to the particular rooms within the building. For example, the rules database 244 may include a plurality of rules established for a particular type of room based on a risk of infection in the type of rooms. For example, operating rooms, where there may be a lot of people coming and going as well open pathways to the body, may have more strict rules dictating tighter control of the environment than a patient room where a patient is recovering from a surgery. The appropriate set of rules may be downloaded to the controller 238 in response to a user identifying the details of the rooms 202, sometimes including available sensors 204, 206, 207 in the rooms, to the controller 238. The user may enter room details at the user interface of the controller 238, through a remote device, or through a web client, as described above. It is contemplated that the sensors 204, 206, 207 may be named or identified such that they are associated with a particular room in the building.

Figure 4:
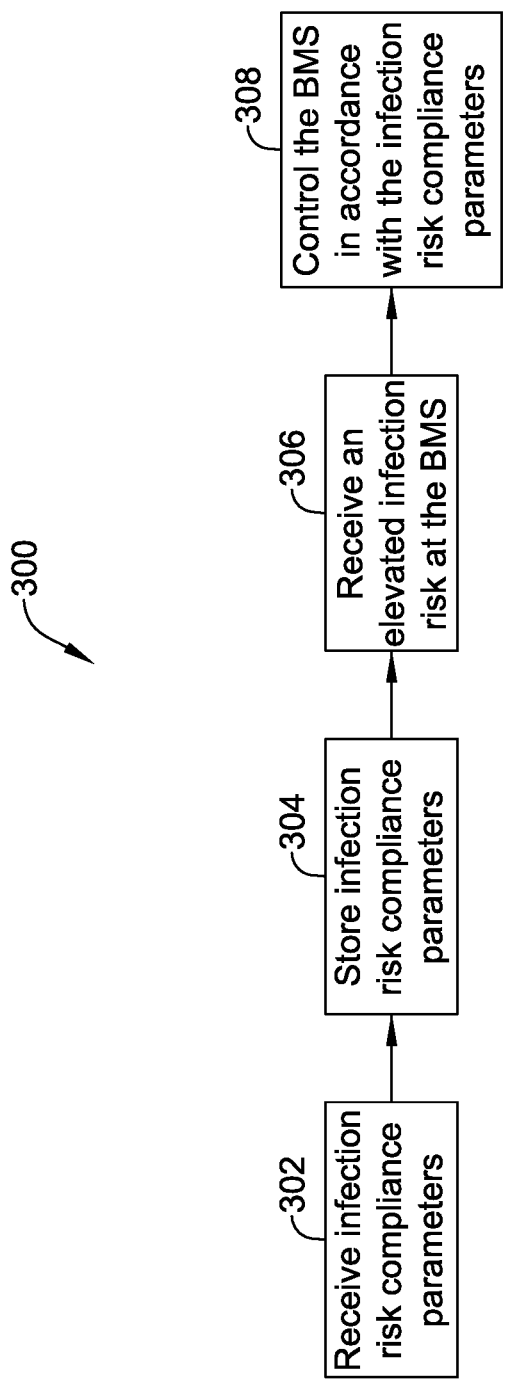
FIG. 4 is a flow chart of an illustrative method for controlling a building management system to help reduce HAI and SSI in the building.

FIG. 4 is a flow chart 300 of an illustrative method for controlling a building management system 234. To begin, infection risk compliance parameters may be received at the building management system 234 and stored in the rules database 244, as shown at block 302. Each hospital may want to define their own infection risk compliance parameters for the various rooms in their facility, based on their own compliance criteria. That is, the infection risk compliance parameters may be tailored to each hospital, and then to different room(s) in the hospital. Then, when the rules are applied, which may take into account the infection risk compliance parameters, the building management system 234 may respond differently in different hospitals.

It is contemplated that the infection risk compliance parameters may be manually entered by a user (e.g., an installer or the medical facility) at the controller 238 (or a remote device 248) or the user may use the controller 238 (or a remote device 248) to send a request to the external server(s) 246 to obtain the rules database, as shown at block 302. Alternatively, or additionally, the controller 238 may automatically request the rules database from the external server(s) 246. Alternatively, or additionally, the controller 238 may be configured to automatically request the most up-to-date rules from the external server(s) 246 at predetermined time schedules. It is further contemplated that additionally, or alternatively, the external server(s) 246 may be configured to automatically send or push revised rules to the controller 238 as the rules are updated.

The infection risk compliance parameters may be stored in the rules database 244 of the building management system 234, as shown at block 304. The infection risk compliance parameters may define, at least in part, how the building management system 234 responds to an elevated infection risk alert from the elevated risk determination system 230. The infection risk compliance parameters, which may be references by the rules, may help dictate how the building management system 234 responds based on the particular elevated infection risk alert, the cause of the elevated infection risk alert, the particular room or room type (e.g., operating room, recovery room, patient room, intensive care unit room, etc.) to which the elevated infection risk alert applies, etc. It is contemplated that the controller 238 may receive infection risk compliance parameters for each of the different room types such that the building management system 234 may be controlled in accordance with the room type when an elevated infection risk occurs in the particular room. In some embodiments, the infection risk compliance parameters may be specific to a particular patient or type of patient. For example, if a high-infection-risk patient is present in a room (e.g. open wound, weak immune system, etc.), a user may input this information to the controller 238, and the rules may cause the controller 238 to control the environment in that room differently than if a low-infection-risk patient (e.g. dehydrated) were in the room.

Referring briefly to FIG. 5, which illustrates an example rules database 400. The rules database 400 illustrated in FIG. 5 is not intended to provide a complete listing of the events which may result in a recommended action or control change in the building management system 234. Instead, the rules database 400 is provided as an example of some illustrative rules that may be created for reducing a patient's risk of infection. Each rule 420a, 420b, 420c, 420d, 420e, 420f (collectively, 420) is shown in a separate row and may include a room type 402, a reason for the elevated infection risk alert 404, one or more actions 406, 408, 410 that may be taken by the building management system 234 to help mitigate the risk, a patient type 412, an alert severity 414, and/or an occupancy of the room 416. The rules 420 may take into consideration compliance parameters (e.g., default values, customized by a hospital, etc.).

In a first example rule 420a, if an elevated particle count is detected, the air changes per hour (ACH) may be increased. In another example rule 420b, if an elevated biological particle count is detected the ACH may be increased and an ultraviolet (UV) light activated to kill the biological particles. In some instances, the UV light may be positioned within an air duct or other portion of the air handling system, although this is not required. In another example rule 420c, if there is elevated traffic in a room (e.g., more people than expected and/or doors opening more than expected) the ACH may be increased and a UV light activated to kill the biological particles. In yet another example rule 420d, if elevated humidity is detected, the ACH may be increased and a dehumidifier activated. In yet another example rule 420e, if the patient condition is indicative of a higher risk for infection, the ACH may be increased, a UV light activated, and the humidity increased. In another example rule 420f, if conditions are indicative of an elevated risk of mold, the ACH may be increased, a dehumidifier activated, and the temperature of the room decreased. In some cases, the ACH may be increased to increase the volume of air, to maintain directional air, and/or to maintain a cleanliness of the air. These are just some examples and are not intended to be limiting.

The action(s) 406, 408, 410 may be specific to the reason for the alert, the room type, the alert severity, and/or the patient type. For example, in some cases, only one action is taken by the building management system 234 while in other cases, multiple actions are taken by the building management system 234. In some embodiments, the action 406, 408, 410 may include automatically adjusting a control parameter of the building management system 234. In other embodiments, a user may be required to approve the control change prior to the controller 238 adjusting the control parameter of the building management system 234. Alternatively, or additionally, a user may be required to verify a condition before a control change is implemented. For example, a user may be required to verify that increase ventilation to a room will not adversely affect the indoor air quality (for example, by bringing in dust from a construction project).

Returning to FIG. 4, the controller 238 of the building management system 234 may be configured to receive an elevated infection risk from the elevated risk determination system 230, as shown at block 306. As described above, the elevated risk determination system 230 monitors the sensor data from each room 202 equipped with sensors 204, 206, 207. When the elevated risk determination system 230 determines a condition in a particular room is consistent with an elevated infection risk, the elevated risk determination system 230 may issue or send an elevated infection risk alert to the building management system 234. In some cases, the elevated infection risk alert may be a binary alert, such as a flag that is raised when the risk of infection crosses a threshold. In other cases, the elevated infection risk alert may present the risk along a scale of risk, from low to high. In some cases, the elevated infection risk alert may include additional information such as what sensed conditions caused or formed the basis of the elevated infection risk alert.

In some instances, the elevated infection risk is then mitigated or addressed by controlling the building management system 234 in accordance with the action(s) 406, 408, 410 defined by rule. The rules may reference one or more infection risk compliance parameters, as shown at block 308. In some cases, the elevated risk determination system 230 may take into account the room type, room location, severity of the alert, and/or other condition or parameter before issuing the elevated infection risk alert. In other cases, the elevated risk determination system 230 may issue an elevated infection risk alert for a particular room, and in response, the controller 238 of the building management system 234 may apply appropriate rules in the rules database 244, along with one or more infection risk compliance parameters, to determine how the controller 238 controls the building management system 234 in that particular room. It is contemplated that the action taken may vary based on a combination of the room type, room location, a severity of the alert, and/or a reason for the alert. In some embodiments, the elevated infection risk alert may cause the controller 238 of the building management system 234 to alert a maintenance crew of required maintenance in or near the particular room which resulted in the elevated infection risk alert. For example, dirty air filters may be detected by an air particle count above a threshold value. In some embodiments, the elevated infection risk alert may cause controller 238 of the building management system 234 to alert a cleaning crew to clean a particular room to help reduce the elevated infection risk alert. For example, images from security cameras can be processed to determine if a particular room has been wiped down by a cleaning crew. Elevated infection risk alerts may be generated if the cleaning is not performed in compliance with cleaning rules. It is contemplated that there may be different cleaning rules for different room types (e.g., operating room, intensive care unit room, recovery room, patient room). It is further contemplated that the clean rules may vary over time for a particular room in accordance with factors that change over time (e.g., occupied, unoccupied, infection risk factors, etc.). In another example, when a low-infection-risk patient is moved out of a room and a high-infection-risk patient in moved into the room, an elevated infection risk alert from the elevated risk determination system 230 may cause the controller 238 of the building management system 234 to control the environment differently and may even schedule an extra cleaning beyond the normal cleaning schedule.

In some embodiments, the building management system 234 may be configured to adjust parameters in other rooms, spaces, and/or corridors to proactively prevent a similar increased risk that has been detected in a particular room. For example, rooms, spaces, and/or corridors adjoining a particular room that has been identified as having conditions consistent with an increased risk of infection may have control parameters manipulated prior to the conditions in said room, space, and/or corridor deteriorating to a level in which an increased risk of infection is identified.

Figure 6:
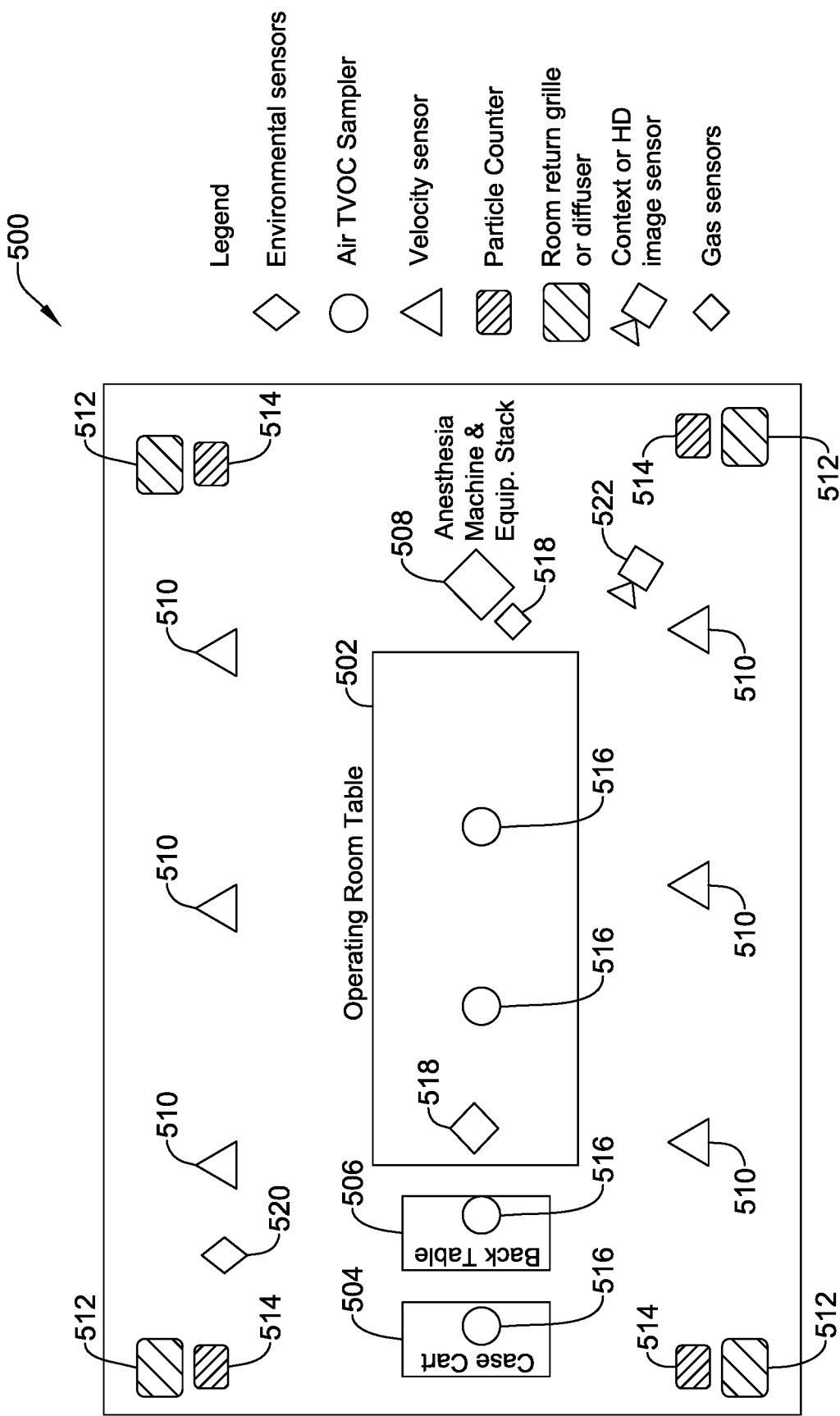
FIGS. 6-8 are schematic views of rooms including an infection risk reduction system.

FIG. 6 illustrates a first dedicated space 500 in which the conditions may be manipulated to reduce the risk of infection. In the illustrated embodiment, the dedicated space 500 may be an operating room or suite. The operating room 500 may include equipment for performing the procedure, such as, but not limited to, an operating table 502, a back table 506, a case cart 504, an anesthesia machine and equipment stack 508, etc. The operating room 500 may further include a plurality of sensors similar in form and function to the sensors 204, 206, 207 described above. The location, arrangement, and number of sensors can vary depending on the application, size of the room, etc. For example, the operating room 500 may include a plurality of velocity sensors 510 positioned about or around the operating table 502. In some cases, the velocity sensors 510 may be positioned between air handling vents 512 (e.g., air inputs, air returns, and/or air recirculating vents). As described above, the air velocity may be manipulated (e.g., increased or decreased) to reduce a patient's risk of infection based on the measure of air velocity at sensors 510. In some embodiments, the operating room 500 may include particle counters 514. It is contemplated that the particle counters 514 may be positioned at or near the air handling vents 512, although this is not required. It is contemplated that a high particle count may indicate a need to replace a filter, increase an air changeover rate, decrease an air changeover rate, etc. In some embodiments, the operating room 500 may include additional air quality sensors, such as, but not limited to total volatile organic compound (TVOC) samplers 516 and/or gas sensors 518.

The operating room 500 may further include one or more environment sensors 520. The environmental sensor(s) may include, but are not limited to temperature sensors, humidity sensors, dew point sensors, air density sensors, etc. In some embodiments, the operating room 500 may further include one or more context or image sensors 522 (which may or may not be high definition). The context sensors 522 can include, but are not limited to monitoring activity (e.g., people entering and/or exiting a room, washing hands, following protocols, etc.), monitoring the location of the occupants of the operating room 500, monitoring the posture of the occupants, monitoring gestures performed by the occupants, monitoring the attire of the occupants, etc.

The data from the sensors 510, 512, 514, 516, 518, 520, 522 may be recorded and analyzed at, for example, a processing unit (not explicitly shown) which may be a building management controller or a separate processing device. The processing unit may issue building control commands based on the sensor data. In some cases, the processing unit may identify a risk of infection (e.g., SSI and/or HAI) based on the sensor data. The processing unit may then adjust a building control parameter (e.g., transmit a change in control parameter to a particular device of the building management system) to mitigate or reduce the risk of infection. Alternatively, or additionally, the processing unit may transmit a recommending to be viewed and/or approved by an appropriate staff member prior to implementing the change. It is contemplated that sensor data may be trended, monitored, displayed, and/or analyzed in real time and viewable on display in the operating room 500 or a location exterior to the room 500. In some cases, the processing unit may be configured to generate compliance reports and/or HAPS SI risk reports (automatically or in response to user input).

Figure 7:
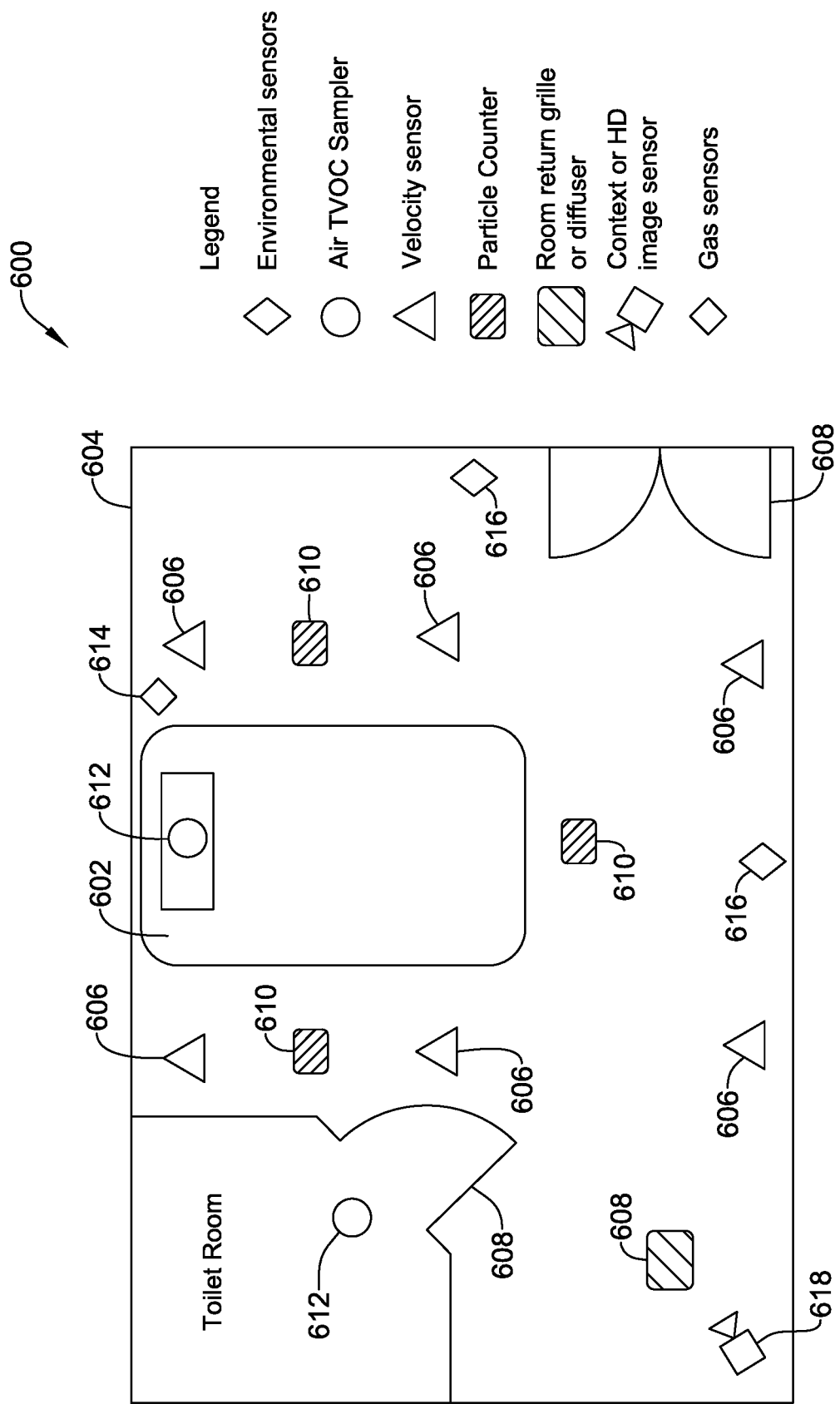

FIG. 7 illustrates another dedicated space 600 in which the conditions may be manipulated to reduce the risk of infection. In the illustrated embodiment, the dedicated space 600 may be a patient room which may include intensive care unit patient rooms and/or other specialized patient rooms. The patient room 600 may include equipment and/or furniture for patient care and/or comfort, such as, but not limited to, a patient bed 602, a toilet room 604, etc. The patient room 600 may further include a plurality of sensors similar in form and function to the sensors 204, 206, 207 described above. The location, arrangement, and number of sensors can vary depending on the application, size of the room, etc. For example, the patient room 600 may include a plurality of velocity sensors 606 positioned about or around the patient bed 602, doors 608, etc. In some cases, the velocity sensors 606 may be positioned between air handling vents 608 (e.g., air inputs, air returns, and/or air recirculating vents). As described above, the air velocity may be manipulated (e.g., increased or decreased) to reduce a patient's risk of infection based on the measured air velocity at sensors 606. In some embodiments, the patient room 600 may include particle counters 610. It is contemplated that the particle counters 610 may be positioned at or near the air handling vents 608, although this is not required. It is contemplated that a high particle count may indicate a need to replace a filter, increase an air changeover rate, decrease an air changeover rate, etc. In some embodiments, the patient room 600 may include additional air quality sensors, such as, but not limited to total volatile organic compound (TVOC) samplers 612 and/or gas sensors 614. While not explicitly shown, the toilet room 604 may include an exhaust system which may be a constant volume exhaust or a variable (e.g., controllable) exhaust.

The patient room 600 may further include one or more environment sensors 616. The environmental sensor(s) may include, but are not limited to temperature sensors, humidity sensors, dew point sensors, air density sensors, etc. In some embodiments, the patient room 600 may further include one or more context or image sensors 618 (which may or may not be high definition). The context sensors 618 can include, but are not limited to monitoring activity (e.g., people entering and/or exiting a room, washing hands, following protocols, etc.), monitoring the location of the occupants of the patient room 600, monitoring the posture of the occupants, monitoring gestures performed by the occupants, monitoring the attire of the occupants, etc.

The data from the sensors 606, 610, 612, 614, 616, 618, may be recorded and analyzed at, for example, a processing unit (not explicitly shown) which may be a building management controller or a separate processing device. The processing unit may issue building control commands based on the sensor data. In some cases, the processing unit may identify a risk of infection (e.g., SSI and/or HAI) based on the sensor data. The processing unit may then adjust a building control parameter (e.g., transmit a change in control parameter to a particular device of the building management system) to mitigate or reduce the risk of infection. Alternatively, or additionally, the processing unit may transmit a recommending to be viewed and/or approved by an appropriate staff member prior to implementing the change. It is contemplated that sensor data may be trended, monitored, displayed, and/or analyzed in real time and viewable on display in the patient room 600 or a location exterior to the room 600. In some cases, the processing unit may be configured to generate compliance reports and/or HAPS SI risk reports (automatically or in response to user input).

Figure 8:
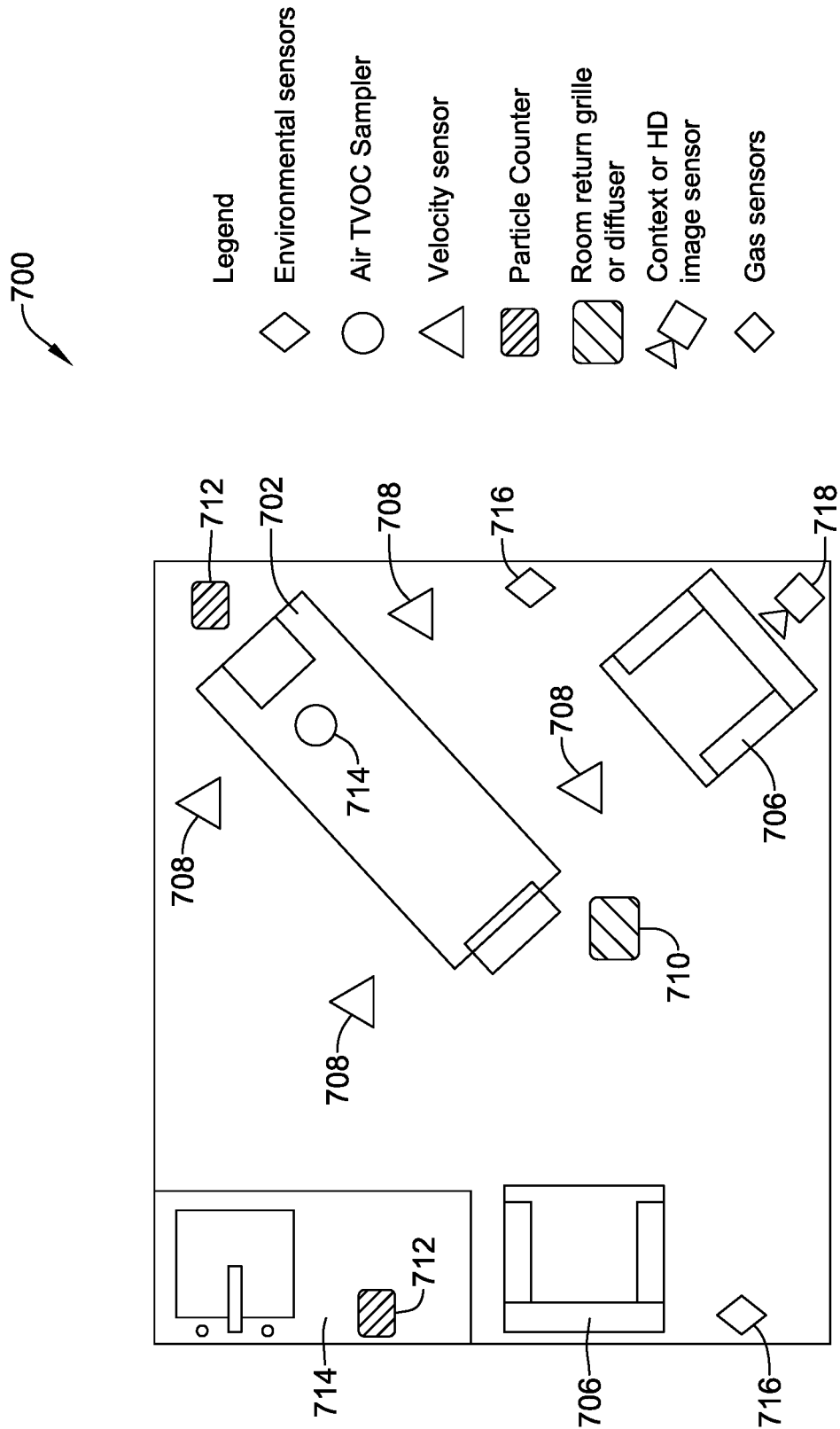

FIG. 8 illustrates another dedicated space 700 in which the conditions may be manipulated to reduce the risk of infection. In the illustrated embodiment, the dedicated space 700 may be a general use space, such as, but not limited a patient examination room. The general use space 700 may include equipment and/or furniture for patient care and/or comfort, such as, but not limited to, an examination table 702, a sink 704, one or more chairs 706, etc. The general use space 700 may further include a plurality of sensors similar in form and function to the sensors 204, 206, 207 described above. The location, arrangement, and number of sensors can vary depending on the application, size of the room, etc. For example, the general use space 700 may include a plurality of velocity sensors 708 positioned about or around the examination table 702, doors (not explicitly shown), etc. In some cases, the velocity sensors 708 may be positioned between air handling vents 710 (e.g., air inputs, air returns, and/or air recirculating vents). As described above, the air velocity may be manipulated (e.g., increased or decreased) to reduce a patient's risk of infection based on the measured air velocity at sensors 708. In some embodiments, the general use space 700 may include particle counters 712. It is contemplated that the particle counters 712 may be positioned at or near the air handling vents 710, although this is not required. It is contemplated that a high particle count may indicate a need to replace a filter, increase an air changeover rate, decrease an air changeover rate, etc. In some embodiments, the general use space 700 may include additional air quality sensors, such as, but not limited to total volatile organic compound (TVOC) samplers 714 and/or gas sensors (not explicitly shown).

The general use space 700 may further include one or more environment sensors 716. The environmental sensor(s) may include, but are not limited to temperature sensors, humidity sensors, dew point sensors, air density sensors, etc. In some embodiments, the general use space 700 may further include one or more context or image sensors 718 (which may or may not be high definition). The context sensors 718 can include, but are not limited to monitoring activity (e.g., people entering and/or exiting a room, washing hands, following protocols, etc.), monitoring the location of the occupants of the general use space 700, monitoring the posture of the occupants, monitoring gestures performed by the occupants, monitoring the attire of the occupants, etc.

The data from the sensors 708, 712, 714, 614, 716, 718, may be recorded and analyzed at, for example, a processing unit (not explicitly shown) which may be a building management controller or a separate processing device. The processing unit may issue building control commands based on the sensor data. In some cases, the processing unit may identify a risk of infection (e.g., SSI and/or HAI) based on the sensor data. The processing unit may then adjust a building control parameter (e.g., transmit a change in control parameter to a particular device of the building management system) to mitigate or reduce the risk of infection. Alternatively, or additionally, the processing unit may transmit a recommending to be viewed and/or approved by an appropriate staff member prior to implementing the change. It is contemplated that sensor data may be trended, monitored, displayed, and/or analyzed in real time and viewable on display in the general use space 700 or a location exterior to the space 700. In some cases, the processing unit may be configured to generate compliance reports and/or HAI/SSI risk reports (automatically or in response to user input).

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A building management system (BMS) for a facility that includes a plurality of regions and a plurality of sensors in the plurality of regions, wherein an elevated infection risk determination system is operatively coupled to the plurality of sensors for determining an elevated infection risk in one or more of the regions of the facility, the building management system comprising:
 a memory for storing one or more first user programmable infection risk compliance parameters for a first region in the facility and one or more second user programmable infection risk compliance parameters that are different from one or more of the first programmable infection risk compliance parameters for a second region in the facility;
 an input port for receiving from the elevated infection risk determination system a first elevated infection risk alert for the first region in the facility and a second elevated infection risk alert for the second region in the facility;
 a control port for providing control commands to one or more building components of the building management system;
 a controller operatively coupled to the memory, the input port and the control port, the controller configured to:
  provide control commands via the control port in response to receiving the first elevated infection risk alert for the first region to help mitigate the elevated infection risk associated with the first elevated infection risk alert in the first region; and
  provide control commands via the control port in response to receiving the second elevated infection risk alert for the second region to help mitigate the elevated infection risk associated with the second elevated infection risk alert in the second region.

2. The building management system (BMS) of claim 1, wherein the one or more first and/or second user programmable infection risk compliance parameters are programmable by one or more users associated with the facility.

3. The building management system (BMS) of claim 2, wherein changing a value of one or more of the first user programmable infection risk compliance parameters for the first region changes how the controller controls the building management system in response to the first elevated infection risk alert for the first region.

4. The building management system (BMS) of claim 2, wherein changing a value of one or more of the second user programmable infection risk compliance parameters for the second region changes how the controller controls the building management system in response to the second elevated infection risk alert for the second region.

5. The building management system (BMS) of claim 1, wherein the plurality of regions correspond to a plurality of zones of the facility.

6. The building management system (BMS) of claim 1, wherein the plurality of regions correspond to a plurality of rooms of the facility.

7. The building management system (BMS) of claim 1, wherein the first elevated infection risk alert comprises an indication of a degree of severity of the first elevated infection risk alert.

8. The building management system (BMS) of claim 7, wherein the controller is configured to provide control commands via the control port that control one or more components of the building management system differently based on the degree of severity of the first elevated infection risk alert.

9. The building management system (BMS) of claim 1, wherein the first elevated infection risk alert comprises an indication of a cause of the first elevated infection risk alert.

10. The building management system (BMS) of claim 9, wherein the controller is configured to provide control commands via the control port that control one or more components of the building management system differently based on the cause of the first elevated infection risk alert.

11. The building management system (BMS) of claim 1, wherein the one or more first user programmable infection risk compliance parameters define one or more rules that affect the control commands that are provided by the controller in response to the first elevated infection risk alert.

12. The building management system (BMS) of claim 1, wherein the plurality of sensors comprise a biohazard sensor.

13. The building management system (BMS) of claim 1, wherein the plurality of sensors comprise one or more of a temperature sensor and a humidity sensor, a pressure sensor.

14. The building management system (BMS) of claim 1, wherein the plurality of sensors comprise a video camera.

15. A method for controlling a building management system of a facility, the building management system including a heating, ventilation, and/or air conditioning (HVAC) system, wherein the facility includes a plurality of regions of different region types serviced by the HVAC system, the method comprising:
receiving one or more first user programmable infection risk compliance parameters for regions of a first region type;
receiving one or more second user programmable infection risk compliance parameters for regions of a second region type, wherein one or more of the second user programmable infection risk compliance parameters is different from one or more of the first user programmable infection risk compliance parameters;
determining a first elevated infection risk alert for a first region in the facility having the first region type based on an output from one or more sensors of the first region and the one or more first user programmable infection risk compliance parameters for regions of the first region type;
determining a second elevated infection risk alert for a second region in the facility having the second region type based on an output from one or more sensors of the second region and the one or more second user programmable infection risk compliance parameters for regions of the second region type;
in response to receiving the first elevated infection risk alert for the first region that has the first region type, controlling one or more components of the HVAC system of the building management system servicing the first region to help mitigate the elevated infection risk associated with the first elevated infection risk alert in the first region; and
in response to receiving the second elevated infection risk alert for the second region that has the second region type, controlling one or more components of the HVAC system of the building management system servicing the second region to help mitigate the elevated infection risk associated with the second elevated infection risk alert in the second region.

16. The method of claim 15, wherein at least some of the one or more first user programmable infection risk compliance parameters for regions of the first region type and at least some of the one or more second user programmable infection risk compliance parameters for regions of the second region type are programmable by one or more users associated with the facility.

17. The method of claim 15, wherein the first elevated infection risk alert comprises an indication of a cause of the first elevated infection risk alert, and controlling one or more components of the HVAC system of the building management system servicing the first region differently based on the cause of the first elevated infection risk alert.

18. A method for controlling a building management system of a facility, wherein the facility includes a plurality of regions and a plurality of sensors including at least one camera in a particular region of the facility, the method comprising:
associating one or more infection risk compliance parameters with the particular region in the facility;
processing images from the at least one camera in the particular region of the facility to determine whether occupant behavior in the particular region of the facility is in compliance with one or more of the infection risk compliance parameters associated with the particular region of the facility;
in response to determining that occupant behavior in the particular region of the facility is not in compliance with one or more of the infection risk compliance parameters associated with the particular region of the facility, issuing an elevated infection risk alert for the particular region of the facility; and
in response to the elevated infection risk alert for the particular region of the facility, controlling the building management system to help mitigate the elevated infection risk in the particular region of the facility.

19. The method of claim 18, wherein the building management system comprises an access control system and/or a security system, and wherein controlling the building management system comprises controlling the access control system and/or security system to help mitigate the elevated infection risk in the particular region of the facility.

20. The method of claim 19, wherein the building management system comprises an HVAC system, and wherein controlling the building management system comprises controlling the HVAC system to help mitigate the elevated infection risk in the particular region of the facility.

* * * * *